United States Patent
Pudil et al.

(10) Patent No.: US 10,537,875 B2
(45) Date of Patent: Jan. 21, 2020

(54) PRECISION RECHARGING OF SORBENT MATERIALS USING PATIENT AND SESSION DATA

(71) Applicant: Medtronic, Inc., Minneapolis, MN (US)

(72) Inventors: Bryant J. Pudil, Plymouth, MN (US); Christopher M. Hobot, Tonka Bay, MN (US); Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 34 days.

(21) Appl. No.: 15/942,229

(22) Filed: Mar. 30, 2018

(65) Prior Publication Data

US 2018/0221852 A1    Aug. 9, 2018

Related U.S. Application Data

(63) Continuation-in-part of application No. 15/364,251, filed on Nov. 29, 2016, now Pat. No. 10,159,957.
(Continued)

(51) Int. Cl.
*B01J 20/06* (2006.01)
*B01J 20/34* (2006.01)
(Continued)

(52) U.S. Cl.
CPC ........ *B01J 20/3475* (2013.01); *A61M 1/1607* (2014.02); *A61M 1/1611* (2014.02);
(Continued)

(58) Field of Classification Search
None
See application file for complete search history.

(56) References Cited

U.S. PATENT DOCUMENTS

| 1,617,288 A | 2/1927 | Kenney |
| 3,608,729 A | 9/1971 | Haselden |

(Continued)

FOREIGN PATENT DOCUMENTS

| CN | 1487853 A | 4/2004 |
| CN | 102573618 | 7/2012 |

(Continued)

OTHER PUBLICATIONS

Blumenkrantz et a., Applications of teh Redy(R) Sorbent System to Hemodialysis and Peritoneal Dialysis, Artif. Organs, Aug. 1979 (Year: 1979).*

(Continued)

*Primary Examiner* — Chester T Barry
(74) *Attorney, Agent, or Firm* — Kenneth Collier; Roger Hahn

(57) ABSTRACT

The invention relates to devices, systems, and methods for recharging zirconium phosphate and/or zirconium oxide in reusable sorbent modules. The devices, systems, and methods provide for precision recharging of the zirconium phosphate and/or zirconium oxide to avoid the need of excess recharge solutions. The devices systems and methods also provide for calculation of the volumes of recharge solution needed for fully recharging the zirconium phosphate and zirconium oxide modules.

14 Claims, 4 Drawing Sheets

Related U.S. Application Data which is a continuation-in-part of application No. 14/722,119, filed on May 26, 2015, now Pat. No. 10,052,612, and a continuation-in-part of application No. 14/722,068, filed on May 26, 2015, now Pat. No. 9,981,245, said application No. 14/722,119 is a continuation-in-part of application No. 14/261,651, filed on Apr. 25, 2014, now Pat. No. 9,895,477, and a continuation-in-part of application No. 14/642,847, filed on Mar. 10, 2015, now Pat. No. 9,974,896, said application No. 14/722,068 is a continuation-in-part of application No. 14/261,651, filed on Apr. 25, 2014, now Pat. No. 9,895,477, and a continuation-in-part of application No. 14/642,847, filed on Mar. 10, 2015, now Pat. No. 9,974,896.

(60) Provisional application No. 61/941,672, filed on Feb. 19, 2014, provisional application No. 61/909,372, filed on Nov. 26, 2013, provisional application No. 62/016,613, filed on Jun. 24, 2014, provisional application No. 62/077,159, filed on Nov. 7, 2014.

(51) Int. Cl.
  *B01J 20/02* (2006.01)
  *A61M 1/16* (2006.01)

(52) U.S. Cl.
  CPC ........ *A61M 1/1654* (2013.01); *A61M 1/1692* (2013.01); *A61M 1/1696* (2013.01); *B01J 20/0211* (2013.01); *B01J 20/0292* (2013.01); *B01J 20/06* (2013.01); *B01J 20/3433* (2013.01); *A61M 2202/0225* (2013.01); *A61M 2205/3303* (2013.01); *A61M 2205/3334* (2013.01)

(56) References Cited

U.S. PATENT DOCUMENTS

| | | |
|---|---|---|
| 3,617,558 A | 11/1971 | Jones |
| 3,669,880 A | 6/1972 | Marantz |
| 3,776,819 A | 12/1973 | Williams |
| 3,840,835 A | 10/1974 | Kussy |
| 3,850,835 A | 11/1974 | Marantz |
| 3,884,808 A | 5/1975 | Scott |
| 3,902,490 A | 9/1975 | Jacobsen et al. |
| 3,989,622 A | 11/1976 | Marantz |
| 4,073,725 A | 2/1978 | Takeuchi |
| 4,094,775 A | 6/1978 | Mueller |
| 4,192,748 A | 3/1980 | Hyden |
| 4,206,054 A | 6/1980 | Moore |
| 4,209,392 A | 6/1980 | Wallace |
| 4,267,047 A * | 5/1981 | Henne ............ B01D 69/04 210/490 |
| 4,376,707 A | 3/1983 | Lehmann |
| 4,460,555 A | 7/1984 | Thompson |
| 4,581,141 A * | 4/1986 | Ash ............ A61M 1/1696 210/321.84 |
| 4,650,587 A | 3/1987 | Polak |
| 4,661,246 A | 4/1987 | Ash |
| 4,684,460 A | 8/1987 | Issautier |
| 4,687,582 A | 8/1987 | Dixon |
| 5,230,702 A | 7/1993 | Lindsay et al. |
| 5,284,470 A | 2/1994 | Beltz |
| 5,302,288 A | 4/1994 | Meidl |
| 5,308,315 A | 5/1994 | Khuri |
| 5,507,723 A | 4/1996 | Keshaviah |
| 5,662,806 A | 9/1997 | Keshaviah et al. |
| 5,770,086 A | 6/1998 | Indriksons |
| 5,849,179 A | 12/1998 | Emerson |
| 5,858,186 A | 1/1999 | Glass |
| 5,944,684 A | 8/1999 | Roberts |
| 6,036,858 A | 3/2000 | Carlsson |
| 6,114,176 A | 9/2000 | Edgson et al. |
| 6,126,831 A | 10/2000 | Goldau et al. |
| 6,521,184 B1 | 2/2003 | Edgson et al. |
| 6,572,769 B2 | 6/2003 | Rajan |
| 6,579,460 B1 | 6/2003 | Willis |
| 6,627,164 B1 | 9/2003 | Wong |
| 6,666,840 B1 | 12/2003 | Falkvall et al. |
| 6,719,745 B1 | 4/2004 | Taylor |
| 6,814,724 B2 | 11/2004 | Taylor |
| 6,818,196 B2 | 11/2004 | Wong |
| 6,861,266 B1 | 3/2005 | Sternby |
| 6,878,258 B2 | 4/2005 | Hughes |
| 6,878,283 B2 | 4/2005 | Thompson |
| 6,878,285 B2 | 4/2005 | Hughes |
| 6,960,179 B2 | 11/2005 | Gura |
| 7,033,498 B2 | 4/2006 | Wong |
| 7,101,519 B2 | 9/2006 | Wong |
| 7,208,092 B2 | 4/2007 | Micheli |
| 7,241,272 B2 | 7/2007 | Karoor |
| 7,276,042 B2 | 10/2007 | Polaschegg |
| 7,326,576 B2 | 2/2008 | Womble et al. |
| 7,435,342 B2 | 10/2008 | Tsukamoto |
| 7,488,447 B2 | 2/2009 | Sternby |
| 7,537,688 B2 | 5/2009 | Tarumi et al. |
| 7,544,300 B2 | 6/2009 | Brugger et al. |
| 7,544,737 B2 | 6/2009 | Puss et al. |
| 7,563,240 B2 | 7/2009 | Gross et al. |
| 7,566,432 B2 | 7/2009 | Wong |
| 7,597,806 B2 | 10/2009 | Uchi |
| 7,794,419 B2 | 7/2010 | Paolini et al. |
| 7,776,210 B2 | 8/2010 | Rosenbaum |
| 7,850,635 B2 | 12/2010 | Polaschegg |
| 7,922,686 B2 | 4/2011 | Childers et al. |
| 7,922,911 B2 | 4/2011 | Micheli |
| 7,947,179 B2 | 5/2011 | Rosenbaum |
| 7,955,290 B2 | 6/2011 | Karoor et al. |
| 7,988,854 B2 | 8/2011 | Tsukamoto |
| 8,002,726 B2 | 8/2011 | Karoor |
| 8,012,118 B2 | 9/2011 | Curtin |
| 8,029,454 B2 | 11/2011 | Kelly et al. |
| 8,066,658 B2 | 11/2011 | Karoor et al. |
| 8,080,161 B2 | 12/2011 | Ding et al. |
| 8,087,303 B2 | 1/2012 | Beavis |
| 8,096,969 B2 | 1/2012 | Roberts |
| 8,180,574 B2 | 5/2012 | Lo et al. |
| 8,187,250 B2 | 5/2012 | Roberts |
| 8,197,439 B2 | 6/2012 | Wang et al. |
| 8,303,532 B2 | 11/2012 | Harnada et al. |
| 8,404,491 B2 | 3/2013 | Ding et al. |
| 8,409,444 B2 | 4/2013 | Wong |
| 8,480,607 B2 | 7/2013 | Davies |
| 8,647,506 B2 | 2/2014 | Wong |
| 8,733,559 B2 | 5/2014 | Wong |
| 8,764,981 B2 | 7/2014 | Ding |
| 8,777,892 B2 | 7/2014 | Sandford |
| 8,889,004 B2 * | 11/2014 | Updyke ............ A61M 1/1696 210/321.71 |
| 9,144,640 B2 | 9/2015 | Pudil |
| 9,254,355 B2 | 2/2016 | Sandford |
| 9,527,015 B2 | 12/2016 | Chau |
| 9,707,329 B2 * | 7/2017 | Merchant ............ A61M 1/1696 |
| 2001/0007931 A1 | 7/2001 | Blatter |
| 2002/0016550 A1 | 2/2002 | Sweeney |
| 2002/0112609 A1 | 8/2002 | Wong |
| 2003/0080059 A1 | 5/2003 | Peterson et al. |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2003/0187479 A1 | 10/2003 | Thong |
| 2004/0019312 A1 | 1/2004 | Childers et al. |
| 2004/0099593 A1 | 5/2004 | DPaolis |
| 2004/0147900 A1 | 7/2004 | Polaschegg |
| 2004/0168963 A1 | 9/2004 | King |
| 2004/0257409 A1 | 12/2004 | Cheok |
| 2005/0006296 A1 | 1/2005 | Sullivan |
| 2005/0056592 A1 | 3/2005 | Braunger |
| 2005/0113796 A1 | 5/2005 | Taylor |
| 2005/0150832 A1 | 7/2005 | Tsukamoto |

(56) References Cited

U.S. PATENT DOCUMENTS

| | | |
|---|---|---|
| 2005/0234354 A1 | 10/2005 | Rowlandson |
| 2005/0274658 A1 | 12/2005 | Rosenbaum |
| 2006/0241543 A1 | 10/2006 | Gura |
| 2007/0007208 A1 | 1/2007 | Brugger et al. |
| 2007/0179431 A1 | 8/2007 | Roberts |
| 2007/0213665 A1 | 9/2007 | Curtin |
| 2008/0006570 A1 | 1/2008 | Gura |
| 2008/0011664 A1 | 1/2008 | Karoor |
| 2008/0051696 A1 * | 2/2008 | Curtin ................. A61M 1/1696 604/29 |
| 2008/0053905 A9 | 3/2008 | Brugger et al. |
| 2008/0241031 A1 | 10/2008 | Li |
| 2009/0020471 A1 | 1/2009 | Tsukamoto |
| 2009/0078636 A1 | 3/2009 | Uchi |
| 2009/0101552 A1 | 4/2009 | Fulkerson |
| 2009/0120864 A1 | 5/2009 | Fulkerson |
| 2009/0216045 A1 | 8/2009 | Singh |
| 2009/0266358 A1 | 10/2009 | Sacristan Rock |
| 2009/0282980 A1 | 11/2009 | Gura |
| 2010/0004588 A1 | 1/2010 | Yeh |
| 2010/0007838 A1 | 1/2010 | Fujimoto |
| 2010/0078381 A1 | 4/2010 | Merchant |
| 2010/0078387 A1 | 4/2010 | Wong |
| 2010/0084330 A1 | 4/2010 | Wong |
| 2010/0100027 A1 | 4/2010 | Schilthuizen |
| 2010/0101195 A1 | 4/2010 | Clements |
| 2010/0102190 A1 | 4/2010 | Zhu et al. |
| 2010/0114012 A1 | 5/2010 | Sandford |
| 2010/0217181 A1 | 8/2010 | Roberts |
| 2010/0224492 A1 | 9/2010 | Ding et al. |
| 2010/0312172 A1 | 12/2010 | Hoffman |
| 2010/0314314 A1 | 12/2010 | Ding |
| 2011/0009798 A1 | 1/2011 | Kelly |
| 2011/0017665 A1 | 1/2011 | Updyke |
| 2011/0048949 A1 | 3/2011 | Ding |
| 2011/0163034 A1 | 7/2011 | Castellarnau |
| 2011/0171713 A1 | 7/2011 | Bluchel |
| 2011/0184340 A1 | 7/2011 | Tan |
| 2011/0272352 A1 | 11/2011 | Braig |
| 2011/0297593 A1 | 12/2011 | Kelly |
| 2012/0018377 A1 | 1/2012 | Tsukamoto |
| 2012/0248017 A1 | 10/2012 | Beiriger |
| 2012/0273354 A1 | 11/2012 | Orhan et al. |
| 2012/0303079 A1 | 11/2012 | Mahajan |
| 2013/0018095 A1 | 1/2013 | Vath |
| 2013/0019179 A1 | 1/2013 | Zhao |
| 2013/0027214 A1 | 1/2013 | Eng |
| 2013/0028809 A1 | 1/2013 | Barton |
| 2013/0116578 A1 | 5/2013 | An |
| 2013/0199998 A1 | 8/2013 | Kelly |
| 2013/0213890 A1 | 8/2013 | Kelly |
| 2013/0213891 A1 | 8/2013 | Karoor |
| 2014/0001112 A1 | 1/2014 | Karoor |
| 2014/0138294 A1 | 5/2014 | Fulkerson |
| 2014/0158588 A1 | 6/2014 | Pudil |
| 2014/0158623 A1 | 6/2014 | Pudil |
| 2014/0190885 A1 | 7/2014 | Meyer |
| 2014/0217028 A1 | 8/2014 | Pudil |
| 2014/0251908 A1 | 9/2014 | Ding |
| 2014/0326671 A1 | 11/2014 | Kelly |
| 2015/0057602 A1 | 2/2015 | Mason |
| 2015/0108069 A1 | 4/2015 | Merchant |
| 2015/0108609 A1 | 4/2015 | Kushida |
| 2015/0144539 A1 | 5/2015 | Pudil |
| 2015/0144542 A1 | 5/2015 | Pudil |
| 2015/0157960 A1 | 6/2015 | Pudil et al. |
| 2015/0238673 A1 | 8/2015 | Gerber |
| 2015/0250937 A1 | 9/2015 | Pudil |
| 2015/0251161 A1 | 9/2015 | Pudil |
| 2015/0251162 A1 | 9/2015 | Pudil |
| 2015/0258266 A1 | 9/2015 | Merchant |
| 2015/0306292 A1 | 10/2015 | Pudil |
| 2015/0367051 A1 | 12/2015 | Gerber |
| 2015/0367052 A1 | 12/2015 | Gerber |
| 2015/0367055 A1 | 12/2015 | Pudil |
| 2015/0367056 A1 | 12/2015 | Gerber |
| 2015/0367057 A1 | 12/2015 | Gerber |
| 2015/0367058 A1 | 12/2015 | Gerber |
| 2015/0367059 A1 | 12/2015 | Gerber |
| 2015/0367060 A1 | 12/2015 | Gerber |
| 2016/0236188 A1 | 8/2016 | Menon |
| 2016/0243299 A1 | 8/2016 | Gerber |
| 2016/0243540 A1 | 8/2016 | Menon |
| 2016/0243541 A1 | 8/2016 | Menon |
| 2017/0087533 A1 | 3/2017 | Hobot |

FOREIGN PATENT DOCUMENTS

| | | | |
|---|---|---|---|
| CN | 105658326 A | | 6/2016 |
| EP | 711182 B1 | | 6/2003 |
| EP | 1592494 B1 | | 6/2009 |
| EP | 2575827 A2 | | 12/2010 |
| EP | 2576453 A2 | | 12/2011 |
| EP | 2446908 | | 5/2012 |
| EP | 1545652 B1 | | 1/2013 |
| EP | 2344220 B1 | | 4/2013 |
| GB | 1451849 A | * | 10/1976 |
| JP | S5070281 A | | 6/1975 |
| JP | S51-55193 | | 5/1976 |
| JP | S51-131393 | | 11/1976 |
| JP | S61164562 | | 7/1986 |
| JP | H4-90963 | | 8/1992 |
| JP | 2981573 | | 11/1999 |
| JP | 2005511250 | | 4/2005 |
| JP | 2007-44602 A | | 2/2007 |
| JP | 200744602 | | 2/2007 |
| JP | 200744602 A | | 2/2007 |
| JP | 2013502987 | | 1/2013 |
| WO | 9532010 A1 | | 11/1995 |
| WO | 0185295 A2 | | 11/2001 |
| WO | 2002043859 | | 6/2002 |
| WO | 2003043677 A2 | | 5/2003 |
| WO | WO 2003041764 | | 5/2003 |
| WO | 2003051422 A2 | | 6/2003 |
| WO | 2004064616 A2 | | 8/2004 |
| WO | 2004062710 A3 | | 10/2004 |
| WO | 2005123230 A2 | | 12/2005 |
| WO | 2007089855 A2 | | 8/2007 |
| WO | 2008075951 A1 | | 6/2008 |
| WO | 2009157877 A1 | | 12/2009 |
| WO | 20090157877 | | 12/2009 |
| WO | 20091578778 A1 | | 12/2009 |
| WO | 2010028860 A1 | | 3/2010 |
| WO | 2010102190 A4 | | 11/2010 |
| WO | 2010141949 | | 12/2010 |
| WO | WO 2011/017215 | | 2/2011 |
| WO | 2013019179 | | 2/2013 |
| WO | 2013019179 A1 | | 2/2013 |
| WO | 2013025957 | | 2/2013 |
| WO | 2013027214 | | 2/2013 |
| WO | 2013028809 A3 | | 2/2013 |
| WO | WO 2013/019179 | | 2/2013 |
| WO | WO 2013/019994 | | 2/2013 |
| WO | WO 2013-025957 | | 2/2013 |
| WO | WO 2013-028809 | | 2/2013 |
| WO | WO 2013019179 | | 2/2013 |
| WO | WO2014121238 A1 | | 2/2013 |
| WO | 1345856 B1 | | 3/2013 |
| WO | 2013019994 A3 | | 4/2013 |
| WO | 2012060700 | | 5/2013 |
| WO | 2013025844 A3 | | 5/2013 |
| WO | 2013101888 | | 7/2013 |
| WO | 2013103607 A1 | | 7/2013 |
| WO | 2013103906 | | 7/2013 |
| WO | WO 2013/103607 | | 7/2013 |
| WO | WO 2013109922 | | 7/2013 |
| WO | 2015060914 | | 4/2015 |
| WO | WO 2015060914 | | 4/2015 |
| WO | WO 2015/126879 | | 8/2015 |
| WO | 2015142624 | | 9/2015 |
| WO | 2015199764 | | 12/2015 |
| WO | 2015199765 | | 12/2015 |
| WO | 2015199863 | | 12/2015 |
| WO | 2015199864 | | 12/2015 |

(56) References Cited

FOREIGN PATENT DOCUMENTS

| WO | WO 2015-199863 | 12/2015 |
|---|---|---|
| WO | WO 2015-199864 | 12/2015 |
| WO | WO 2015199765 | 12/2015 |
| WO | WO 2016/191039 | 12/2016 |

OTHER PUBLICATIONS

Office Action in Japanese Application No. 2016-553344, dated Apr. 24, 2018.
[NPL608] PCT/US2015/019901 Written Opinion dated May 27, 2016.
[NPL610] PCT/US2015/019901 International Search Report dated Jun. 5, 2015.
[NPL720] PCT/US2015/019901 International Search Report and Written Opinion dated Jun. 5, 2015.
[NPL722] PCT/US2015/032494 International Preliminary Report on Patentablity dated Dec. 27, 2016.
[NPL756] European Search Report and Supplemental Search Report in European Application No. 14865374.4 dated Jun. 12, 2017.
[NPL696] PCT/US2015/032485 Written Opinion dated May 9, 2016.
[NPL591] PCT/US2016/030320 Written Opinion dated Jul. 27, 2016.
[NPL602] Office Action in App. No. JP 2016-515476 dated Dec. 26, 2016.
[NPL605] PCT/US2015/032494 Written Opinion dated Nov. 19, 2015.
[NPL606] PCT/US2015/032494 International Search Report dated Nov. 19, 2015.
[NPL607] PCT/US2015/019901 International Preliminary Report on Patentability dated May 27, 2016.
[NPL609] PCT/US2015/019901 Written Opinion dated Jun. 5, 2015.
[NPL611] PCT/US2015/032485 International Preliminary Report on Patentability dated May 11, 2016.
[NPL612] PCT/US2015/032485 International Preliminary Report on Patentability dated May 11, 2016.
[NPL613] PCT/US20115/032485 International Preliminary Report on Patentability dated May 11, 2016.
[NPL615] PCT/US2016/030304 Written Opinion dated Jul. 27, 2016.
[NPL616] PCT/US2016/030312 Written Opinion dated Jul. 28, 2016.
[NPL617] PCT/US2016/030312 International Search Report dated Jul. 28, 2016.
[NPL618] PCT/US2016/030319 International Search Report dated Jul. 27, 2016.
[NPL619] PCT/US2016/030319 Written Opinion dated Jul. 27, 2016.
[NPL603] Japanese Patent Publication No. S50-70281A.
[NPL621] PCT/US2016/030320 International Search Report dated Jul. 28, 2016.
[NPL623] PCT/US2015/032485 Written Opinion dated Oct. 16, 2016.
[NPL634] PCT/US2016/030320 International Preliminary Report on Patentability, dated Apr. 20, 2017.
PCT/US2016/030319_IPRP.
[NPL721] PCT/US2015/019901 International Preliminary Report on Patentability dated May 27, 2016.
PCT/US2016/030304_IPRP.
[NPL622] PCT/US2015/032485 Written Opinion dated Oct. 16, 2015.
Search Report in EP App. No. 15752771, dated Nov. 22, 2017.
[NPL584] Office Action in App. No. AU 2015280604 dated Apr. 8, 2016.
[NPL601] Wester et al., A regenerable postassium and phosphate sorbent system to enhance dialysis efficacy and device portability: an in vitro study Nephrol Dial Transplant (2013) 28: 2364-2371 Jul. 3, 2013.
[NPL3] PCT/US2015/019901 International Search Report and Written Opinion dated Jun. 5, 2015.
[NPL494] John Wm Agar: Review: Understanding sorbent dialysis systems, Nephrology, vol. 15, No. 4, Jun. 2010, pp. 406-411.
[NPL614] PCT/US2016/030304 International Search Report dated Jul. 27, 2016.
[NPL620] PCT/US2016/030320 Written Opinion dated Jul. 28, 2016.
[NPL626] PCT/US2015/032485 International Search Report and Written Opinion dated Oct. 16, 2015.
[NPL2] PCT/US2015/032492 International Search Report dated Nov. 19, 2015.
[NPL6] PCT/US2015/032492 Written Opinion dated Nov. 19, 2015.
[NPL162] International Search Report from PCT/US2012/051946 dated Mar. 4, 2013.
[NPL163] U.S. Appl. No. 61/526,209.
[NPL1] PCT/US2014/065950 International Search Report and Written Opinion dated Feb. 24, 2015.
[NPL238] PCT Application, PCT/US20013/020404, filed Jan. 4, 2013.
[NPL240] U.S. Appl. No. 13/836,973, filed Mar. 15, 2013.
[NPL241] U.S. Appl. No. 14/259,655, filed Apr. 23, 2014.
[NPL242] U.S. Appl. No. 14/259,589, filed Apr. 23, 2014.
[NPL243] U.S. Appl. No. 13/757,693, filed Jan. 4, 2013.
[NPL244] U.S. Appl. No. 13/836,079, filed Mar. 15, 2013.
[NPL245] U.S. Appl. No. 14/240,129, filed Aug. 22, 2013.
[NPL247] U.S. Appl. No. 13/835,735, filed Mar. 15, 2013.
[NPL4] PCT/US2015/016270 International Search Report and Written Opinion dated Jun. 5, 2015.
[NPL548] PCT/US15/18587 International Preliminary Report on Patentability dated Jun. 6, 2016.
[NPL590] PCT/US2016/030319 Written Opinion dated Jul. 27, 2016.
[NPL5] PCT/US2015/016273 International Search Report and Written Opinion dated Jun. 9, 2015.
[NPL7] PCT/US2015/020046 International Search Report and Written Opinion dated Jun. 29, 2015.
[NPL8] PCT/US2015/020044 International Search Report Written Opinion dated Jun. 30, 2015.
[NPL] European Search Report App 14865374.4, dated Jun. 12, 2017.
European Search Report for App. No. 18153940.4, dated Jun. 12, 2018.
Search Report for EP App. No. 17203984.4, dated Mar. 29, 2018.
European Search Report for App. No. 15812081.6, dated Mar. 8, 2018.
European Search Report for EP App. No. 15811326.6, dated Feb. 14, 2018.
European Search Report for EP App. No. 15812413.1, dated Feb. 2, 2018.
[NPL10] Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.
Office Action for European App. No. 17203968.7, dated Nov. 14, 2019.

* cited by examiner

PRECISION RECHARGING OF SORBENT MATERIALS USING PATIENT AND SESSION DATA

CROSS-REFERENCE TO RELATED APPLICATIONS

This application is a continuation-in-part application of U.S. patent application Ser. No. 15/364,251 filed Nov. 29, 2016, now U.S. Pat. No. 10,159,957, which is a continuation-in-part application of U.S. patent application Ser. No. 14/722,119 filed May 26, 2015 now U.S. Pat. No. 10,052,612, and U.S. patent application Ser. No. 14/722,068 filed May 26, 2015, now U.S. Pat. No. 9,981,245. U.S. patent application Ser. No. 14/722,119 and U.S. patent application Ser. No. 14/722,068 are each continuation-in-part applications of U.S. patent application Ser. No. 14/261,651 filed Apr. 25, 2014, now U.S. Pat. No. 9,895,477, and U.S. patent application Ser. No. 14/642,847 filed Mar. 20, 2015, now U.S. Pat. No. 9,974,896. U.S. patent application Ser. No. 14/261,651 plains the benefit of and priority to U.S. Provisional Patent Application No. 61/941,672 filed Feb. 19, 2014 and U.S. Provisional Patent Application No. 61/909,372 filed Nov. 26, 2013. U.S. patent application Ser. No. 14/642,847 claims the benefit of and priority to U.S. Provisional Patent Application No. 62/016,613 filed Jun. 24, 2014 and U.S. Provisional Patent Application No. 62/077,159 filed Nov. 7, 2014.

FIELD OF THE INVENTION

The invention relates to devices, systems, and methods for recharging zirconium phosphate and/or zirconium oxide in reusable sorbent modules. The devices, systems, and methods provide for precision recharging of the zirconium phosphate and/or zirconium oxide to avoid the need of excess recharge solutions. The devices systems and methods also provide for calculation of the volumes of recharge solution needed for fully recharging the zirconium phosphate and zirconium oxide modules.

BACKGROUND

Zirconium phosphate is used in sorbent dialysis to remove waste and unwanted solutes including ammonium, potassium, calcium, and magnesium ions from dialysate. Zirconium oxide can be used to remove phosphate ions from dialysate. The zirconium phosphate and zirconium oxide are generally packaged in a sorbent cartridge. Usually, sorbent cartridges are discarded and replaced after use. The discarded sorbent cartridges are broken down and the zirconium phosphate and zirconium oxide are separated from the other sorbent materials. Because zirconium phosphate and zirconium oxide are expensive and rechargeable, sorbent re-processors treat the recovered materials with chemical solutions. The recycling process requires transporting the materials to reprocessing facilities and involves laborious recycling steps in addition to recharging the sorbent materials. Further, the sorbent material cannot be immediately reused, and must be added to a new sorbent cartridge and repackaged for sale. Conventional methods drive up costs and infrastructure requirements, and increase complexity and waste.

Different patients may require differing dialysate bicarbonate levels for effective treatment. For example, alkalotic patients require a dialysate bicarbonate level lower than other patients. The bicarbonate level of the dialysate is generally controlled by the addition sodium bicarbonate, which acts as a buffer. Bicarbonate ions in the dialysate are in equilibrium with carbon dioxide. The zirconium phosphate effluent pH is the main driver in determining the bicarbonate/carbon dioxide ratio. A lower zirconium phosphate effluent pH will produce more $pCO_2$ which can result in dialysate entering the dialyzer at too low a pH, potentially causing hemolysis. High $pCO_2$ can also cause bubbles to form in the dialysate which can potentially be transferred to the patient. The excess $CO_2$ can be removed by a degasser, such as a membrane contactor degasser, a vacuum degasser, or any other device capable of removing $CO_2$ from solution. A higher zirconium phosphate effluent pH will result in higher bicarbonate concentration, requiring less bicarbonate addition to the dialysate, but may not be usable in treatment of all patients.

Known recharging systems do not control the volume of chemical solutions used in recharging the zirconium phosphate and zirconium oxide, and instead simply treat the materials with enough recharging chemicals to ensure complete recharging. Complete recharging of the sorbent materials is generally used to cover worst case situations to avoid ammonia breakthrough in patients with high levels of urea or other ions. Complete recharging of the sorbent materials in each case is wasteful and more costly than recharging the sorbent materials only to the point necessary for a future dialysis session. Recharging zirconium phosphate or zirconium oxide in this fashion results in the use of higher volumes of recharging chemicals than may be necessary.

Hence, there is a need for systems and methods that can recharge zirconium phosphate in a zirconium phosphate sorbent module and/or zirconium oxide in a reusable zirconium oxide sorbent module in a precise and efficient manner. There is a need for systems and methods that can more precisely match a recharge process for zirconium phosphate and/or zirconium oxide with actual cartridge need and usage, thus eliminating extra expense, time, money, and chemical usage. There is also a need for systems and method that can customize the dialysate bicarbonate levels by controlling the zirconium phosphate effluent pH. There is further a need for systems and methods that can control the zirconium phosphate recharging process to create a zirconium phosphate module having a desired effluent pH. The need extends to systems and methods for determining a desired zirconium phosphate effluent pH based on the needs of the patient and system. There is also a need for systems and methods that can calculate the amount of recharging solutions necessary for recharging the zirconium phosphate and/or zirconium oxide.

SUMMARY OF THE INVENTION

The first aspect of the invention relates to a method. In any embodiment, the method can include recharging a sorbent material within a sorbent module by pumping one or more recharge solutions through the sorbent module; wherein a volume and/or a concentration of the one or more recharge solutions is set based on one or more patient parameters and/or one or more dialysis session parameters for a patient and/or dialysis session using the sorbent module.

In any embodiment, the sorbent module can contain zirconium phosphate; the one or more patient parameters can include at least one from a group consisting of: pre-dialysis patient potassium, calcium, magnesium, bicarbonate and urea levels, patient weight, patient volume, patient residual kidney function, patient acidotic state, an average number of dialysis sessions per week, and an average dialysis session length; and the one or more dialysis session parameters can include at least one from a group consisting of: dialysate flow rate, blood flow rate, dialyzer size, dialyzer type, dialysis time, ultrafiltration rate, a potassium, calcium, magnesium, and bicarbonate dialysis prescription, whether ammonia breakthrough occurred, whether a pH alarm occurred, fluid removed during a session, total volume treated, starting water quality, URR target, URR achieved, clearance, whether a blood leak occurred, and whether a hypotensive episode occurred.

In any embodiment, the sorbent module can contain zirconium oxide; the one or more patient parameters can include at least one from a group consisting of: patient weight, patient volume, patient residual kidney function, an average number of dialysis sessions per week, and an average dialysis session length; and the one or more dialysis session parameters can include at least one from a group consisting of: dialysate flow rate, blood flow rate, dialyzer size, dialyzer type, dialysis time, ultrafiltration rate, a potassium, calcium, magnesium, and bicarbonate dialysis prescription, whether ammonia breakthrough occurred, whether a pH alarm occurred, fluid removed during a session, total volume treated, starting water quality, URR target, URR achieved, clearance, whether a blood leak occurred, and whether a hypotensive episode occurred.

In any embodiment, the sorbent module can contain zirconium phosphate, and wherein the one or more patient parameters and/or one or more dialysis session parameters include a total cation and total $CO_2$ pumped through the sorbent module during a prior dialysis session.

In any embodiment, the total cation and total $CO_2$ pumped through the sorbent module can be obtained from any one or more of: (a) direct measurement of total cations and total $CO_2$ in a dialysate flow path during the prior dialysis session; (b) estimation of total cations and total $CO_2$ based on patient weight; (c) estimation of total cations and total $CO_2$ based on a dialysis prescription; (d) estimation of total cations and total $CO_2$ based on pre-dialysis patient cation measurements and/or pre-dialysis patient total $CO_2$ measurements; (e) estimation of total cations and total CO2 based on a number of previous dialysis sessions; or (f) combinations thereof.

In any embodiment, the step of recharging the zirconium phosphate can comprise pumping between 5.0 and 6.0 millimoles of sodium in the one or more recharge solutions per total milliequivalents of total cations pumped through the sorbent module during the prior dialysis session.

In any embodiment, the step of recharging the zirconium phosphate can comprise pumping between 0.3 and 1.0 millimoles of acetate in the one or more recharge solutions per millimole of total $CO_2$ pumped through the sorbent module during the prior dialysis session.

In any embodiment, the sorbent module can contain zirconium oxide, and the one or more patient parameters and/or one or more dialysis session parameters can include a total phosphate pumped through the sorbent module during a prior dialysis session.

In any embodiment, the total phosphate pumped through the sorbent module during the prior dialysis session can be obtained from direct measurement of phosphate in a dialysate flow path during the prior session, estimated based on phosphate bleed from zirconium phosphate used in the prior dialysis session and pre-dialysis patient phosphate measurements; or estimated based on a total phosphate pumped through the sorbent cartridge in a number of previous dialysis sessions.

In any embodiment, the step of recharging the zirconium oxide can comprise pumping between 6.0 and 7.5 moles of sodium hydroxide in the one or more recharge solutions per mole of phosphate pumped through the sorbent module during the prior dialysis session.

In any embodiment, the one or more patient parameters and/or one or more dialysis session parameters can include an estimated duration to a next dialysis session for the patient.

In any embodiment, the sorbent module can contain zirconium phosphate, and the volume of the one or more recharge solutions can be set using an equation $V_r = v*Q*t*(C_{NH4}+C_K+C_{Ca}+C_{Mg}+(a*C_{HCO3}+b))$; wherein Vr is the volume of the one or more recharge solutions, Q is a time averaged volume flow rate into the sorbent module, t is a session time, $C_{NH4}$, $C_K$, $C_{Ca}$, $C_{Mg}$, and $C_{HCO3}$ are average concentrations of ammonium ions, potassium ions, calcium ions, magnesium ions and bicarbonate ions entering the sorbent module, a and b are variables related to a pH of the zirconium phosphate, and v is a variable specific to a recharge process being used.

The features disclosed as being part of the first aspect of the invention can be in the first aspect of the invention, either alone or in combination, or follow a preferred arrangement of one or more of the described elements.

The second aspect of the invention is drawn to a system. In any embodiment, the system can comprise a recharging flow path; the recharging flow path comprising one or more recharge solution sources; the one or more recharge solution sources fluidly connectable to an inlet of a sorbent module containing at least one sorbent material; and at least one pump for pumping one or more recharge solutions from the one or more recharge solution sources through the sorbent module; and a control system, the control system setting a volume and/or concentration of the one or more recharge solutions pumped through the sorbent module necessary to recharge the sorbent material within the sorbent module based on one or more patient parameters and/or one or more dialysis session parameters for a patient and/or dialysis session using the sorbent module.

In any embodiment, the sorbent module can contain zirconium phosphate, and the one or more recharge solution sources can comprise a brine source, a water source, and a disinfectant source.

In any embodiment, the sorbent module can contain zirconium oxide, and the one or more recharge solution sources can comprise a base source, a water source, and a disinfectant source.

In any embodiment, the system can comprise a second recharging flow path; the second recharging flow path comprising one or more recharge solution sources fluidly connectable to an inlet of a second sorbent module containing at least one sorbent material; and at least a second pump for pumping one or more recharge solutions from the one or more recharge solution sources through the sorbent module; and the control system can set a volume and/or concentration of the one or more recharge solutions pumped through the second sorbent module necessary to recharge the sorbent material within the second sorbent module based on the one or more patient parameters and/or one or more dialysis session parameters for the patient and/or dialysis session using the sorbent module.

In any embodiment, the sorbent module can contain zirconium phosphate, the one or more patient parameters can include at least one from a group consisting of: pre-dialysis patient potassium, calcium, magnesium, bicarbonate and urea levels, patient weight, patient volume, patient residual kidney function, an average number of dialysis sessions per week, patient acidotic state, and an average dialysis session length; and the one or more dialysis session parameters include at least one from a group consisting of: dialysate flow rate, blood flow rate, dialyzer size, dialyzer type, dialysis time, ultrafiltration rate, a potassium, calcium, magnesium, and bicarbonate dialysis prescription, whether ammonia breakthrough occurred, whether a pH alarm occurred, fluid removed during a session, total volume treated, starting water quality, URR target, URR achieved, clearance, whether a blood leak occurred, and whether a hypotensive episode occurred.

In any embodiment, the sorbent module can contain zirconium oxide; the one or more patient parameters can include at least one from a group consisting of: patient weight, patient volume, patient residual kidney function, an average number of dialysis sessions per week, and an average dialysis session length; and the one or more dialysis session parameters can include at least one from a group consisting of: dialysate flow rate, blood flow rate, dialyzer size, dialyzer type, dialysis time, ultrafiltration rate, a potassium, calcium, magnesium, and bicarbonate dialysis prescription, whether ammonia breakthrough occurred, whether a pH alarm occurred, fluid removed during a session, total volume treated, starting water quality, URR target, URR achieved, clearance, whether a blood leak occurred, and whether a hypotensive episode occurred.

In any embodiment, the sorbent module can contain zirconium phosphate, and the control system can set the volume and/or concentration of the one or more recharge solutions based on a total cation and total $CO_2$ pumped through the sorbent module during a prior dialysis session.

In any embodiment, the sorbent module can contain zirconium oxide, and the control system can set the volume and/or concentration of the one or more recharge solutions based on a total phosphate pumped through the sorbent module during a prior dialysis session.

The features disclosed as being part of the second aspect of the invention can be in the second aspect of the invention, either alone or in combination, or follow a preferred arrangement of one or more of the described elements.

DETAILED DESCRIPTION OF THE INVENTION

Figure 1:
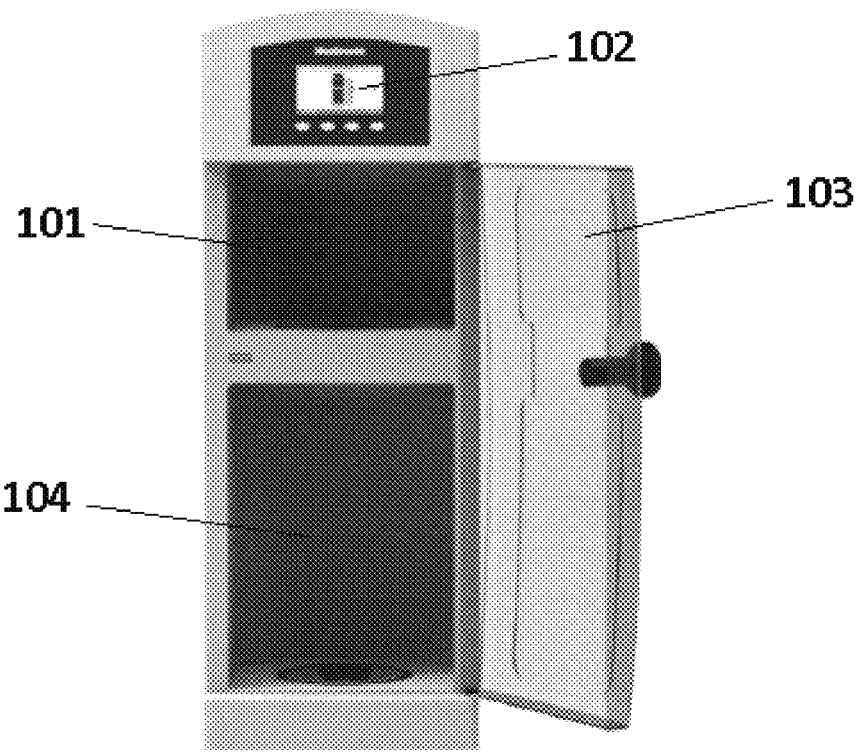
FIG. 1 shows a recharger for recharging a zirconium phosphate module and/or a zirconium oxide module.

Unless defined otherwise, all technical and scientific terms used have the same meaning as commonly understood by one of ordinary skill in the art.

The articles "a" and "an" are used to refer to one or to over one (i.e., to at least one) of the grammatical object of the article. For example, "an element" means one element or over one element.

The term "acid concentration" refers to the number of moles of an acid dissolved in a given volume of water.

The term "acid solution" refers to an aqueous solution having a pH less than 7.

An "acid source" is a fluid or concentrate source from which an acid solution can be obtained.

The term "ammonia breakthrough" refers to ammonia in a fluid exiting a sorbent cartridge.

The term "amount of cations removed by the zirconium phosphate module in a dialysis session" refers to the total number of moles of potassium, calcium, magnesium, ammonium, and other cations adsorbed by zirconium phosphate in the zirconium phosphate module during dialysis therapy.

The term "average dialysis session length" refers to the amount of time a patient spends undergoing dialysis in a normal dialysis session.

The term "average number of dialysis sessions per week" refer to the number of times a patient undergoes dialysis treatment during a normal treatment schedule.

The term "base concentration" refers to the number of moles of a base dissolved in a given volume of water.

The term "base solution" refers to an aqueous solution having a pH of greater than 7.

A "base source" is a fluid or concentrate source from which a base solution can be obtained.

"Blood flow rate" refers to an amount of blood pumped through an extracorporeal circuit in a given period of time.

The term "blood leak" refers to blood of the patient crossing a dialyzer membrane into a dialysate.

The term "brine source" refers to a source of a solution of salts and/or buffers containing solutes used in recharging a sorbent material. In certain embodiments, the brine source can contain a sodium salt, acetic acid, sodium acetate, or combinations thereof.

The term "buffer solution" refers to an aqueous solution containing a weak acid and the conjugate base of the weak acid.

The term "clearance" refers to a rate at which solutes pass through a dialyzer membrane.

The term "comprising" includes, but is not limited to, whatever follows the word "comprising." Use of the term indicates the listed elements are required or mandatory but that other elements are optional and may be present.

The term "concentration" refers to an amount of a solute per a given volume of a solvent.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The terms "control," "controlling," or "controls" refers to the ability of one component to direct the actions of a second component.

A "control system" can be a combination of components that act together to maintain a system to a desired set of performance specifications. The control system can use processors, memory and computer components configured to interoperate to maintain the desired performance specifications. The control system can also include fluid or gas control components, and solute control components as known within the art to maintain the performance specifications.

The term "desired initial therapy zirconium phosphate effluent pH" refers to an initial zirconium phosphate effluent pH during therapy set or determined, at least in part, on the needs and capabilities of the system and patient.

The terms "determining" and "determine" refer to ascertaining a particular state or desired state of a system or variable(s).

"Dialysate flow rate" refers to an amount of dialysate pumped through a dialysate flow path in a given period of time.

The term "dialysis prescription" refers to dialysis parameters intended to be used during a dialysis session. In certain embodiments, a "dialysis prescription" can refer to an intended concentration of one or more solutes in the dialysate used during treatment. For example, a calcium dialysis prescription can refer to the intended calcium concentration of the dialysate during treatment.

A "dialysis session" is time period that a patient is treated by dialysis, hemodialysis, hemofiltration, ultrafiltration, or other blood fluid removal therapy.

A "dialysis session parameter" is any data or condition relating to a specified dialysis session.

The term "dialysis time" refers to the length of time of a specific dialysis session.

The term "dialyzer size" refers to a surface area of a dialyzer membrane in a dialyzer.

The term "dialyzer type" refers to whether a specific dialyzer is a high-flux or low-flux dialyzer. The type can include other characteristics of properties of the dialyzer in addition to flux such as efficiency and membrane types. Efficiency properties such as membrane size (surface area), porosity, thickness, internal fiber diameters, and design (wavelike, straight fiber) are contemplated.

A "disinfectant source" can refer to a fluid source capable of destroying or removing biological contaminants.

The term "direct measurement" refers to using a sensor or other system to determine one or more parameters.

The term "duration to a next dialysis session" refers to an estimated length of time between the end of a first dialysis session for a patient and the beginning of a second dialysis session for the same patient.

"Estimated," to "estimate," or "estimation" refer to a determination of one or more parameters indirectly using one or more variables.

The term "fluidly connectable" refers to the ability of providing for the passage of fluid, gas, or combination thereof, from one point to another point. The ability of providing such passage can be any connection, fastening, or forming between two points to permit the flow of fluid, gas, or combinations thereof. The two points can be within or between any one or more of compartments of any type, modules, systems, components, and rechargers.

The term "fluidly connected" refers to a particular state such that the passage of fluid, gas, or combination thereof, is provided from one point to another point. The connection state can also include an unconnected state, such that the two points are disconnected from each other to discontinue flow. It will be further understood that the two "fluidly connectable" points, as defined above, can from a "fluidly connected" state. The two points can be within or between any one or more of compartments, modules, systems, components, and rechargers, all of any type.

The term "fluid removed during a session" refers to the total amount of fluid removed from the blood of a patient during a dialysis session.

A "heater" is a component capable of raising the temperature of a substance, container, or fluid.

The term "heating" or to "heat" refers to raising the temperature of a material.

The term "hypotensive episode" refers to an instance of low blood pressure in a patient during treatment.

The term "inlet" of a sorbent module can refer to a portion of a sorbent module through which fluid, gas, or a combination thereof can be drawn into the sorbent module.

The term "initial therapy zirconium phosphate effluent pH" refers to the pH of a fluid exiting a zirconium phosphate sorbent module at or near the beginning of therapy.

The term "mixing" or to "mix" generally refers to causing or more fluids from any source to combine together. For example, "mixing" can include laminar or turbulent flow at a location in a fluid line or a junction. Another example of "mixing" can include receiving one or more fluids in a component configured to receive fluids from one or multiple sources and to mix the fluids together in the component. Additionally, mixing can refer to the dissolution of a solid or solids with a fluid, wherein the solid or solids is dissolved in the fluid.

The term "necessary to recharge" a sorbent material refers to an amount of one or more recharge solutions required to result in a sorbent material with a specified functional capacity. In certain embodiments the specified functional capacity can be near 100% or can be lower depending on the needs of a patient.

The term "number of previous dialysis sessions" can refer to any number of dialysis sessions for a patient. The number of previous dialysis sessions can be 1, 2, 3, or more dialysis sessions.

A "patient" or "subject" is a member of any animal species, preferably a mammalian species, optionally a human. The subject can be an apparently healthy individual, an individual suffering from a disease, or an individual being treated for a disease. In certain embodiments, the patient can be a human, sheep, goat, dog, cat, mouse or any other animal.

The term "patient acidotic state" refers to a pH level in the blood of a patient.

A "patient parameter" is any data that gives relevant information about the health status and therapy requirements of a patient.

"Patient residual kidney function" is a measurement of how well a kidney of a patient is working as compared to a healthy individual.

"Patient volume" refers to the total amount of water in a patient.

"Patient weight" refers to the mass of a patient.

The term "pH alarm" refers to an indication that the pH of a fluid is outside of a predetermined range.

The term "pH of the zirconium phosphate" refers to the negative log of the concentration of hydrogen ions absorbed onto a given amount of zirconium phosphate.

"Phosphate bleed" refers to an amount of phosphate ions originally present as zirconium phosphate that leak into a fluid pumped through a sorbent cartridge.

"Pre-dialysis patient cation measurements" refer to determinations of cation levels in a patient prior to a dialysis session.

"Pre-dialysis patient total $CO_2$ measurements" refer to determinations of total $CO_2$ levels in a patient prior to a dialysis session, and can include carbon dioxide levels, bicarbonate levels, and carbonate levels.

"Pre-dialysis patient phosphate measurements" refer to a determination of a phosphate level in a patient prior to a dialysis session.

The term "pre-dialysis patient level," when referring to specific solutes or materials, refers to the concentration of the solutes or materials in the blood of a patient prior to a dialysis session.

The term "pump" refers to any device that causes the movement of fluids or gases by applying suction or pressure.

The terms "pumping," "pumped," or to "pump" refers to moving a fluid, a gas, or a combination thereof with a pump.

A "receiving compartment" is a space within a recharger into which a sorbent module to be recharged is placed.

A "recharge solution" is a solution containing appropriate ions for recharging a specific sorbent material. A recharge solution can be a single solution containing all necessary ions for recharging a sorbent material. Alternatively, the recharge solution can contain some of the ions for recharging the sorbent material, and one or more other recharge solutions can be used to recharge the sorbent material.

A "recharge solution source" is any fluid or concentrate source from which a recharge solution can be obtained.

"Recharging" refers to treating a sorbent material to restore the functional capacity of the sorbent material so as to put the sorbent material back into a condition for reuse or use in a new dialysis session. In some instances, the total mass, weight and/or amount of "rechargeable" sorbent materials remain the same. In some instances, the total mass, weight and/or amount of "rechargeable" sorbent materials change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged."

A "recharging flow path" is a path through which fluid can travel while recharging sorbent material in a reusable sorbent module.

The term "salt concentration," as used herein, refers to the number of moles of a sodium salt dissolved in a given volume of water.

A "salt solution" refers to an aqueous solution containing dissolved sodium and counter ions.

A "salt source" is a fluid or concentrate source from which a salt solution can be obtained.

The term "sequential order" refers to two or more events occurring at different times, as opposed to simultaneously.

The term "session time" refers to a length of time of a dialysis session, from the beginning of dialysis treatment of a patient to the end of the dialysis treatment.

The terms "set based at least in part on" or "set based on" refer to a calculation of a parameter value, wherein the value is a function of at least one other variable.

A "sorbent cartridge module" or "sorbent module" means a discreet component of a sorbent cartridge. Multiple sorbent cartridge modules can be fitted together to form a sorbent cartridge of two, three, or more sorbent cartridge modules. In some embodiments, a single sorbent cartridge module can contain all of the necessary materials for dialysis. In such cases, the sorbent cartridge module can be a "sorbent cartridge." The "sorbent cartridge module" or "sorbent module" can contain any material for use in sorbent dialysis and may or may not contain a "sorbent material" or adsorbent. In other words, the "sorbent cartridge module" or "sorbent module" generally refers to the use of the "sorbent cartridge module" or "sorbent module" in sorbent-based dialysis, e.g., REDY (REcirculating DYalysis), and not that a "sorbent material" is necessarily contained in the "sorbent cartridge module" or "sorbent module."

The term "sorbent material" refers to a material capable of removing specific solutes from a fluid. In certain embodiments, the sorbent material can be zirconium oxide or zirconium phosphate.

The phrase "specific to a recharge process being used" can refer to one or more variables that are used to recharge a sorbent material. In certain embodiments, the variables can include a composition of a recharge solution, concentrations of one or more solutes in the recharge solution, temperature of the recharge solution, or flow rate of the recharge solution.

The term "specified temperature" is a temperature range calculated or determined prior to recharging a zirconium phosphate module.

The term "starting water quality" can refer to the quality of the water used in preparing an initial dialysate for a dialysis session. In certain embodiments, the starting water quality can refer to an amount of solutes dissolved in the water used in preparing the initial dialysate.

A "static mixer" is a component configured to receive fluids from one or multiple sources and to mix the fluids together. The static mixer may include components that agitate the fluids to further mixing.

The term "temperature sensor" refers to a device for measuring the temperature of a gas or liquid in a vessel, container, or fluid line.

The term "time averaged volume flow rate" can refer to a volume of fluid moved per unit time averaged over a dialysis session.

The term "total cation" can refer to an amount of cations in a dialysate throughout a dialysis session.

"Total $CO_2$" can refer to the total amount of carbon dioxide, bicarbonate ions, and carbonate ions in a dialysate throughout a dialysis session.

The term "total phosphate" refers to the total amount of phosphate ions in a dialysate throughout a dialysis session.

The term "total volume treated" refers to a total amount of fluid pumped through a sorbent cartridge or sorbent module during dialysis treatment.

The term "ultrafiltration rate" refers to an amount of fluid removed from the blood of a patient in a given period of time.

"Urea reduction ratio" or "URR" refers to the amount by which the urea level of a patient is reduced during treatment. The URR can be expressed as 1 minus the ratio of the patient's ending urea level over the patient's starting urea level.

"URR achieved" refers to the urea reduction level actually resulting from a dialysis session.

"URR target" refers to an intended urea reduction ratio during a dialysis session.

A "valve" is a device capable of directing the flow of fluid or gas by opening, closing or obstructing one or more pathways to control whether or not the fluid or gas to travel in a particular path. One or more valves that accomplish a desired flow can be configured into a "valve assembly."

The term "volume" refers to a three-dimensional amount of space occupied by a material.

A "water source" is a fluid source from which water can be obtained.

"Zirconium oxide" is a sorbent material that removes anions from a fluid, exchanging the removed anions for different anions. Zirconium oxide may also be referred to as hydrous zirconium oxide, "Zirconium phosphate" is a sorbent material that removes cations from a fluid, exchanging the removed cations for different cations Zirconium Phosphate Recharging The invention is drawn to systems and methods for recharging and reusing zirconium phosphate and/or zirconium oxide in reusable sorbent modules. FIG. 1 illustrates a recharger for recharging zirconium phosphate or zirconium oxide in a sorbent module. The recharger includes at least a first receiving compartment 101 for receiving a sorbent module. The receiving compartment 101 has a sorbent module inlet and a sorbent module outlet (not shown) fluidly connectable to an inlet and outlet of a sorbent module (not shown). Door 103 controls access to the receiving compartment 101. A user interface 102 can receive information from a user for controlling the recharge process. The recharger can optionally include a second receiving compartment 104 for receiving a second sorbent module, containing the same or a different sorbent material for concurrent recharging of sorbent materials. The recharger can include any number of receiving compartments for receiving multiple sorbent modules or various combinations of sorbent modules. The recharger can have 1, 2, 3, 4, 5, or more receiving compartments for recharging any number of sorbent modules. The recharger can be fluidly connectable to one or more recharge solution sources through a recharging flow path. Pumps and valves (not shown) control the movement of fluid from the recharge solution sources through the zirconium phosphate module.

Zirconium phosphate is recharged by pumping one or more solutions containing acids, bases, and sodium salts through the zirconium phosphate module. The hydrogen and sodium ions in the recharge solutions displace potassium, calcium, magnesium, ammonium, and other ions from either the dialysate or source water that are bound and adsorbed by the zirconium phosphate during use. The recharged zirconium phosphate with sodium and hydrogen ions can be used during dialysis to remove cation solutes from the used dialysate. Zirconium oxide can be recharged by pumping one or more solutions containing a hydroxide base through the zirconium oxide sorbent module. The hydroxide ions can displace phosphate ions that are bound and adsorbed by the zirconium oxide during use.

Figure 2:
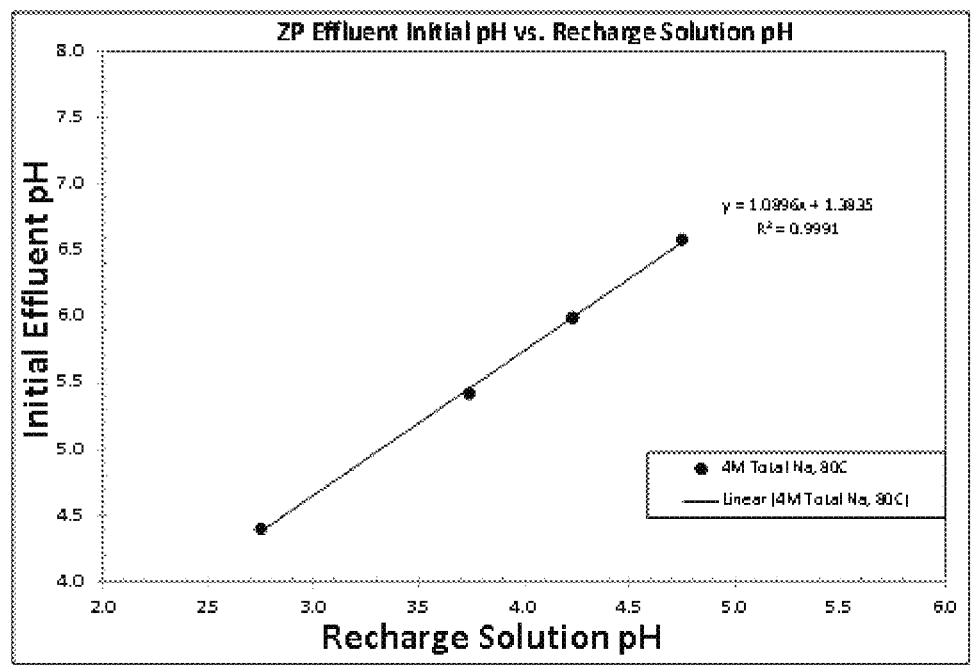
FIG. 2 shows a graph of the initial zirconium phosphate effluent pH as a function of the recharge solution pH.

The initial therapy zirconium phosphate effluent pH depends on the ratio of hydrogen to sodium ions on the zirconium phosphate. FIG. 2 illustrates the effect of the recharge solution pH on the initial therapy zirconium phosphate effluent pH. The recharge solutions in FIG. 2 each contain mixtures of sodium chloride, sodium acetate, and acetic acid. The total sodium concentration in each recharge solution is 4 M, with the ratio of sodium acetate to acetic acid varied to control the pH. As illustrated in FIG. 2, the pH of the recharge solution controls the initial therapy zirconium phosphate effluent pH. One of ordinary skill in the art will understand the initial therapy zirconium phosphate effluent pH can be controlled by adjusting the pH of the recharge solution to result in a desired initial therapy zirconium phosphate effluent pH. The initial therapy zirconium phosphate effluent pH is controlled by altering a ratio of hydrogen ions to sodium ions in the zirconium phosphate. A lower pH recharge solution increases the hydrogen ion to sodium ion ratio on the recharged zirconium phosphate and lowers the initial therapy zirconium phosphate pH. A higher pH recharge solution decreases the hydrogen ion to sodium ion ratio on the recharged zirconium phosphate and increases the initial therapy zirconium phosphate effluent pH. The zirconium phosphate effluent pH can be customized based on the needs of the user by controlling the pH of the recharge solution.

Figure 3:
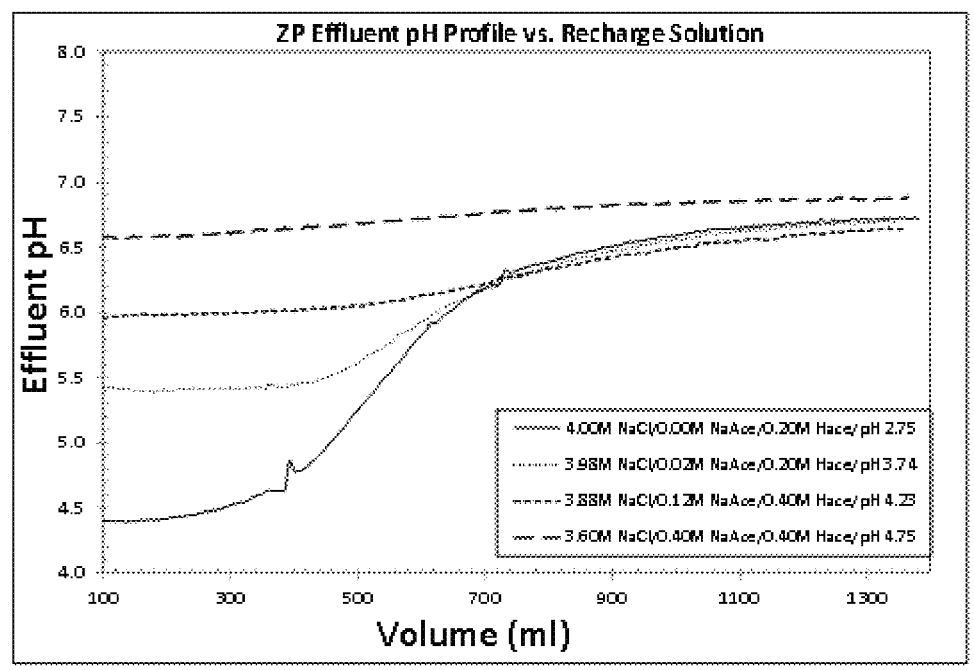
FIG. 3 shows a graph of the zirconium phosphate effluent pH as a function of an amount of fluid passed through the zirconium phosphate module for recharge solutions having various concentrations of acid, base, and salt.

FIG. 3 illustrates the zirconium phosphate effluent pH as a function of the volume of dialysate pumped through the zirconium phosphate module during dialysis. As illustrated in FIG. 3, the initial zirconium phosphate effluent pH is determined by the recharge solutions used. The pH profile of the zirconium phosphate depends on the mass of the zirconium phosphate and the mass of bicarbonate pumped through the zirconium phosphate module. With a high zirconium phosphate mass, and a low bicarbonate mass pumped through the zirconium phosphate, the initial zirconium phosphate effluent pH may be maintained for an entire therapy session. The zirconium phosphate acts like a buffer and as more bicarbonate is pumped through the zirconium phosphate, the buffer capacity becomes exceeded and the pH will start to increase. Without being limited to any theory of invention, the final pH plateau may be related to the composition and pH of the spent dialysate that is pumped through the zirconium phosphate module. However, the initial therapy zirconium phosphate effluent pH is dependent on the pH of the recharge solution.

Table 1 provides non-limiting examples of recharge solutions and the resulting initial therapy zirconium phosphate effluent pH. In each case, the recharge solution was heated to 80° C. prior to use. As shown in Table 1, a higher ratio of sodium acetate to acetic acid results in a higher recharge solution pH, and therefore a higher initial therapy zirconium phosphate effluent pH. The relative amounts of acid, base, and sodium salt can be set to generate a recharge solution having the desired pH.

TABLE 1

| Solution | Total Na (M) | NaCl (M) | NaAce (M) | HAce (M) | pH | Initial Effluent PH |
|---|---|---|---|---|---|---|
| 1 | 4.00 | 4.00 | 0.00 | 0.20 | 2.75 | 4.40 |
| 2 | 4.00 | 3.98 | 0.02 | 0.20 | 3.74 | 5.42 |
| 3 | 4.00 | 3.88 | 0.12 | 0.40 | 4.23 | 5.99 |
| 4 | 4.00 | 3.60 | 0.40 | 0.40 | 4.75 | 6.58 |

Each of the recharge solutions in Table 1 are combinations of sodium chloride, sodium acetate, and acetic acid. One of skill in the art will understand other buffer combinations can be used in place of sodium acetate and acetic acid, including sodium citrate and citric acid, glycolic acid and sodium glycolate, propionic acid and sodium propionate, phosphoric acid and sodium phosphate, or any combination thereof. The relative amounts of sodium chloride and buffer to achieve a desired initial therapy zirconium phosphate effluent pH will depend on the pKa of the acid used and can be varied as needed.

The zirconium phosphate module effluent pH affects the amount of bicarbonate needed during dialysis. Urease in the sorbent cartridge converts urea to carbon dioxide and ammonium ions. The carbon dioxide produced is in equilibrium with bicarbonate in the dialysate. The carbon dioxide must be removed from the dialysate by a degasser prior to the dialysate entering the dialyzer. The degasser can be any type of degasser known in the art for use in dialysis systems. A high zirconium phosphate effluent pH during therapy drives the equilibrium towards bicarbonate formation, resulting in too much bicarbonate in the dialysate for safe treatment. A low zirconium phosphate effluent pH during therapy drives the equilibrium towards carbon dioxide formation, requiring addition of bicarbonate to the dialysate and placing a high burden on the degasser. One type of degasser suitable for removing carbon dioxide is a membrane contactor. A membrane contactor is a dual chamber device with a hydrophobic microporous membrane separating the chambers. The hydrophobic microporous membrane allows gas transport without allowing water transport across the membrane. Liquid containing gas—in this case $CO_2$—is passed on one side of the membrane and either inert gas or a vacuum is applied to the chamber on the opposite side of the membrane. $CO_2$ is transported from the liquid by diffusion. Another example of a degasser is a vacuum degasser. A vacuum degasser is a chamber in which a vacuum can be applied, and which is fluidly connected to a liquid containing gas to be removed. The liquid is sprayed or atomized in the vacuum chamber. The high surface area of the liquid droplets allows efficient removal of the gas. One of skill in the art will understand that any device capable of removing $CO_2$ from the dialysate can be used. The zirconium phosphate effluent pH can be controlled by the pH of the recharge solution to meet the needs of the patient and system. The zirconium phosphate effluent pH is a function of the pH, pKa, buffer capacity, sodium chloride level, and temperature of the recharge solution. As described, a control system can automatically determine the volumes of each component needed to achieve a desired initial therapy zirconium phosphate effluent pH based on each of the factors.

A zirconium phosphate effluent pH of about 6.5 allows greater than 95% of patients to be treated with a dialysate bicarbonate concentration of 25 mM. At a higher pH, fewer patients can be treated. For example, only about 40% of patients can be treated with a zirconium phosphate effluent pH of 6.9 and a dialysate bicarbonate level of 25 mM. At a very low pH, too much acid is added to the dialysate by the zirconium phosphate, and additional bicarbonate will be necessary to keep the dialysate pH within a safe range, and a degasser is needed to remove carbon dioxide. The initial therapy zirconium phosphate effluent pH can be set at any value capable of generating safe dialysate, including between 4.0 and 6.9. A dialysate with a lower pH places a higher burden on the degasser.

Any combination of acid, base, and sodium salt capable of generating a recharge solution within the desired pH range can be used in recharging the zirconium phosphate. Non-limiting examples of acids and bases include sodium acetate and acetic acid, sodium citrate and citric acid, glycolic acid and sodium glycolate, propionic acid and sodium propionate, phosphoric acid and sodium phosphate, or any combination thereof. One of skill in the art will understand the relative amounts of acid and base needed to generate a recharge solution with a desired pH will vary with the pKa of the acid. The relative volumes of the acid and base can be varied based on the pKa of the particular acid and base used. For example, a recharge solution with 3.1 M sodium chloride, 0.9 M sodium acetate, and 0.6 M acetic acid has a pH of 4.6, which will generate a zirconium phosphate effluent pH of 6.5.

As described, the zirconium phosphate effluent pH during therapy controls the equilibrium between carbon dioxide and bicarbonate in the dialysate. Carbon dioxide and bicarbonate in the dialysate generally comes from two sources, the conversion of urea to carbon dioxide and any bicarbonate added to the dialysate. To minimize the amount of additional bicarbonate required, the zirconium phosphate effluent pH can be set to a higher value, at least for patients that can be effectively treated with a higher dialysate bicarbonate level. The higher zirconium phosphate effluent pH during therapy drives the bicarbonate/carbon dioxide equilibrium towards bicarbonate formation, retaining bicarbonate generated from the urea removed from the patient.

A control system in the recharger can determine the optimal initial therapy zirconium phosphate effluent pH for a patient based on the patient's pre-treatment bicarbonate and urea levels. For alkalotic patients, a lower initial therapy zirconium phosphate effluent pH can be selected to minimize the amount of bicarbonate formed from the patient's urea. For other patients, a higher initial therapy zirconium phosphate effluent pH can be selected to generate a higher amount of bicarbonate from the patient's urea, reducing the additional bicarbonate needed and minimizing the burden on the degasser. Alternatively, a user interface can be provided, with the user directly inputting the desired initial therapy zirconium phosphate effluent pH.

The control system can be any component capable of monitoring and affecting the states of the recharger. The control system can use processors, memory and computer components to carry out the functions described. The control system is in communication with the pumps and valves of the recharging flow paths and can control the pumps and valves in accordance with stored instructions. The control system is also in communication with various sensors in the recharging flow paths. The control system receives data from the sensors and controls the pumps and valves of the recharging flow path on the basis of the data in accordance with stored instructions. Factors affecting the desired initial therapy zirconium phosphate effluent pH, such as patient pre-treatment urea and bicarbonate levels can be communicated to the control system by any means known in the art. The control system can automatically determine the optimal recharging solution pH using mathematical algorithms or look-up tables and operate the pumps and valves of the recharging flow paths to control the recharging process.

Figure 4:
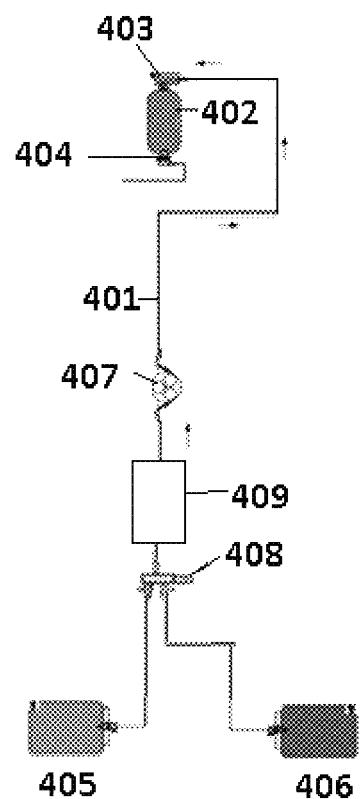
FIG. 4 is a recharging flow path for recharging a zirconium phosphate module with two recharge solution sources.

FIG. 4 illustrates a non-limiting embodiment of a recharging flow path 401 for customization of a recharging solution. A zirconium phosphate module 402 can connect to the recharging flow path 401 through zirconium phosphate inlet 403 and zirconium phosphate outlet 404. Pump 407 provides a driving force for moving fluids through the recharging flow path 401. A salt or brine source 405, containing a salt solution such as sodium chloride or mixtures of sodium chloride and sodium acetate, and an acid source 406 containing an acid solution, such as acetic acid, are fluidly connected to the recharging flow path 401. Valve 408 determines the amount of each recharge solution that enters the recharging flow path 401 to generate a recharge solution having a specified acid concentration, base concentration, and salt concentration, and can be controlled by the control system. Sodium chloride and/or sodium acetate from brine source 405 is pumped through the recharging flow path 401 to the zirconium phosphate module 402. Acid from acid source 406 can be pumped into the recharging flow path 401 at a ratio to the sodium chloride and sodium acetate based on the desired recharge solution pH. For example, acetic acid from acid source 406 can be metered in to the sodium chloride and/or sodium acetate in recharging flow path 401 at a specified rate to control the pH of the resulting recharge solution. A higher sodium chloride to acid ratio will result in a recharge solution at a higher pH, while a lower sodium chloride to acid ratio will result in a recharge solution at a lower pH. The control system can automatically control valve 408 to control the ratio of sodium chloride to acid. Alternatively, the acid source 406 can contain a buffer solution, such as sodium acetate and acetic acid, and the control system can control the ratio of sodium chloride and buffer to control the recharge solution pH. A static mixer 409 can be included to ensure complete mixing of the acid and sodium solutions. Alternatively, the acid and sodium solutions can be mixed through the mixing of the two fluid streams in the recharging flow path 401. One of skill in the art will understand that different pump and valve arrangements can be used with the system illustrated in FIG. 4. For example, the brine source 405 and acid source 406 can be connected to the recharging flow path 401 through separate pumps, allowing simultaneous addition of sodium chloride and acid to the recharging flow path 401.

Alternatively, a system as illustrated in FIG. 4 can have sodium chloride and an acid in a first recharge solution source, with a base solution, such as sodium hydroxide, in a base source. The sodium chloride and acid can be pumped through the zirconium phosphate module, with the base solution metered in to generate a recharge solution with the desired pH in situ.

The recharging flow path 401 in FIG. 4 can also recharge the zirconium phosphate module 402 by addition of recharging solutions in a sequential order. The acid solution from acid source 406 can be pumped through the zirconium phosphate module 402 first, followed by sodium chloride and sodium acetate from brine source 405. The initial acid solution will generate a zirconium phosphate module 402 at a low pH, and the later addition of sodium chloride and sodium acetate will raise the pH as sodium ions displace the hydrogen ions initially adsorbed by the zirconium phosphate. The resulting zirconium phosphate effluent pH will depend on the amount of sodium chloride and sodium acetate pumped through the zirconium phosphate module 402 in the second step. The control system can control the sodium chloride and sodium acetate addition to generate a zirconium phosphate module 402 with the desired initial therapy zirconium phosphate effluent pH. A pH sensor (not shown) can be placed in the zirconium phosphate effluent to determine the zirconium phosphate effluent pH, and the sodium chloride can be stopped when the pH sensor reads the desired pH. The concentration and amount of sodium chloride and sodium acetate pumped through the zirconium phosphate module 402 will control the initial therapy zirconium phosphate effluent pH after recharging. Alternatively, the sodium chloride and sodium acetate can be pumped through the zirconium phosphate module 402 first, followed by the acid.

Figure 5:
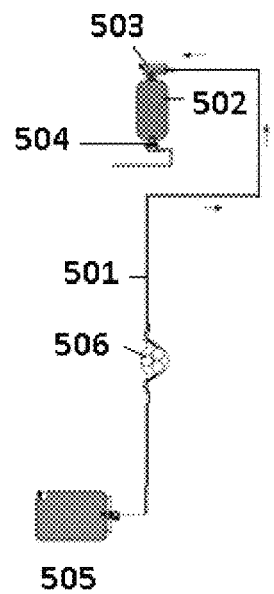
FIG. 5 is a recharging flow path for recharging a zirconium phosphate module with a single recharge solution source.

FIG. 5 illustrates a recharging flow path 501 with a single recharge solution source 505 containing a sodium salt and buffer. A zirconium phosphate module 502 can be fluidly connected to the recharging flow path 501 through zirconium phosphate inlet 503 and zirconium phosphate outlet 504. Pump 506 provides a driving force for moving fluids through the recharging flow path 501. Recharge solution source 505 is fluidly connected to the recharging flow path 501. A recharge solution in recharge solution source 505 at the desired recharge solution pH can be pumped through the zirconium phosphate module 502 to recharge the zirconium phosphate. To alter the initial therapy zirconium phosphate effluent pH, the pH of the recharge solution can be altered. The user can add solid or concentrated sources of an acid, a base, a salt, or combinations thereof, to control the pH of the recharge solution to generate a recharge solution having a specified acid concentration, base concentration, and salt concentration. The control system can inform the user of the correct amounts of acid, base, or salt to add to the recharge solution source 505. Alternatively, a separate source of acid, base, or salt can be included in the recharger, and the system can automatically add the correct amount to the recharge solution source 505 based to generate a recharge solution with the desired pH. For example, a recharge solution with a pH of 4.6 can be placed in the recharge solution source 505 and used for the majority of patients. For severely alkalotic patients, the system or user can add a predetermined amount of acid to lower the recharge solution pH. To reduce the amount of bicarbonate needed during therapy, the system or user can add a predetermined amount of base to raise the recharge solution pH.

Figure 7:
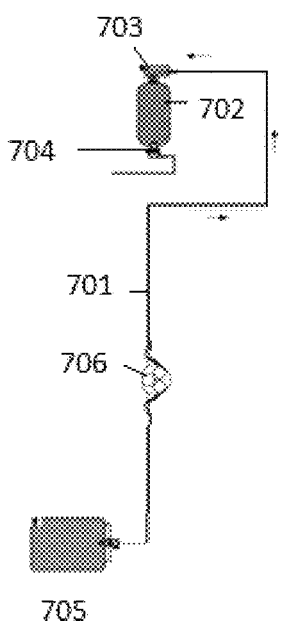
FIG. 7 is a recharging flow path for recharging a zirconium oxide sorbent module.

FIG. 7 illustrates a non-limiting embodiment of a recharging flow path 701 for recharging zirconium oxide in a reusable zirconium oxide sorbent module 702. The zirconium oxide sorbent module 702 can be fluidly connected to the recharging flow path 701 through zirconium oxide module inlet 703 and zirconium phosphate module outlet 704. Pump 706 provides a driving force for moving fluids through the recharging flow path 701. Recharge solution source 705 is fluidly connected to the recharging flow path 701 and can be a base source. The recharge solution source 705 can contain sodium hydroxide at a specified concentration. A control system (not shown) can set the volume of sodium hydroxide pumped through the zirconium oxide sorbent module 702 based on one or more patient parameters and/or one or more dialysis session parameters.

One of skill in the art will understand the recharging flow paths illustrated in FIGS. 4-5 and 7 can include additional fluid sources. A water source can provide water for flushing and rinsing of the zirconium phosphate module and/or zirconium oxide module before and after recharging. A water source can also provide in-line dilution of any of the recharge solutions, allowing a more concentrated recharge solution in the recharge solution sources. A disinfectant source can provide a disinfection solution for disinfecting the zirconium phosphate and/or zirconium oxide module prior to recharging. The disinfection solution can be any solution capable of disinfecting the zirconium phosphate and/or zirconium oxide sorbent module, including a peracetic acid solution, a citric acid solution, or any other disinfectant.

The recharger can include multiple recharging flow paths for recharging multiple sorbent modules. For instance, a single recharger can include two or more recharging flow paths for recharging two or more zirconium phosphate sorbent modules or two or more zirconium oxide sorbent modules. Additionally, a single recharger can include both a zirconium phosphate recharging flow path and a zirconium oxide recharging flow path for recharging both a zirconium phosphate sorbent module and a zirconium oxide sorbent module. One or more recharge solution sources can be shared by both recharging flow paths, or separate recharge solution sources can be used in each flow path.

The total volume of recharge solution needed to recharge the zirconium phosphate depends on the amount of cations removed by the zirconium phosphate in the previous dialysis session and the amount of total $CO_2$ fed through the zirconium phosphate during the previous dialysis session, which in turn depend on a number of patient and/or dialysis parameters. Patient parameters affecting the amount of cations removed by the zirconium phosphate and the amount of $CO_2$ fed through the zirconium phosphate include pre-dialysis patient potassium, calcium, magnesium, bicarbonate and urea levels; patient weight, patient volume, patient residual kidney function, an average number of dialysis sessions per week, patient acidotic state, and an average dialysis session length. Dialysis parameters affecting the amount of cations removed from the zirconium phosphate include dialysate flow rate, blood flow rate, dialyzer size, dialyzer type, dialysis time, ultrafiltration rate, a potassium, calcium, magnesium, and bicarbonate dialysis prescription, whether ammonia breakthrough occurred, whether a pH alarm occurred, fluid removed during a session, total volume treated, starting water quality, URR target, URR achieved, clearance, whether a blood leak occurred, and whether a hypotensive episode occurred.

The total volume of recharge solution needed to recharge the zirconium oxide depends on the amount of phosphate removed by the zirconium oxide in the previous dialysis session, which in turn can depend on a number of patient and/or dialysis parameters. Patient parameters affecting the amount of phosphate removed by the zirconium oxide include patient weight, patient volume, patient residual kidney function, an average number of dialysis sessions per week, and an average dialysis session length. Dialysis parameters affecting the amount of phosphate removed by the zirconium oxide include dialysate flow rate, blood flow rate, dialyzer size, dialyzer type, dialysis time, ultrafiltration rate, a potassium, calcium, magnesium, and bicarbonate dialysis prescription, whether ammonia breakthrough occurred, whether a pH alarm occurred, fluid removed during session, total volume treated, starting water quality, URR target, URR achieved, clearance, whether a blood leak occurred, and whether a hypotensive episode occurred.

Usage of a zirconium phosphate module and/or a zirconium oxide module by a patient can be tracked with an RFID tag, barcode, or other tracking device. The control system can receive any one or more of the patient parameters influencing the amount of recharge solution needed and determine the necessary volume of the recharge solution for recharging the zirconium phosphate module and/or zirconium oxide module. In certain embodiments, the control system can receive patient and dialysis parameters from the prior usage and history of the sorbent cartridge and patient to determine the necessary volume of the recharge solution for recharging the zirconium phosphate module and/or zirconium oxide module. The control system can use all prior history and usage of the patient and sorbent modules, or can use the prior history and usage over any specified length of time. In certain embodiments, the control system can use the patient and dialysis parameters from a previous week, month, year, or longer period of time.

A tracking component, such as an RFID tag or bar code, can be affixed to the sorbent modules, and automatically read by the control system at various times, including prior to dialysis, after dialysis, prior to recharging, and after recharging. A single reader can read and track the sorbent modules at each stage of use, or separate readers can be included with the rechargers and dialysis systems to track usage of the sorbent modules. The tracking system can track which patients used the sorbent modules and the dialysis parameters that affect the amount of recharge solutions necessary to recharge the sorbent modules. The parameters can be communicated to the control system, which can then determine the amount of recharge solution necessary through mathematical algorithms, look-up tables or a combination thereof.

Generally, about 5.5 millimoles of sodium in the recharge solution is required per total milliequivalents of cations (ammonium+potassium+calcium+magnesium) that are fed through the zirconium phosphate during therapy in order to recover greater than 90% of the original capacity of the zirconium phosphate. Lower moles of sodium are needed per mole of cations loaded on the zirconium phosphate for full recharging at elevated temperatures, and less recharge solution is needed with a higher recharge solution concentration. A higher amount of sodium may be needed if the recharging is conducted at room temperature. The recharge solution can have any amount of sodium ions relative to the amount of cations loaded on the zirconium phosphate, including sodium ions between 5 and 15 times greater than the amount of cations loaded on the zirconium phosphate. In certain embodiments, the total millimoles of sodium pumped through the zirconium phosphate module during recharging can be between 5.0 and 15.0 millimoles of sodium per milliequivalent of cations, between 5.0 and 10.0 millimoles of sodium per milliequivalent of cations, between 5.0 and 6.0 millimoles of sodium per milliequivalent of cations, between 7.0 and 12.0 millimoles of sodium per milliequivalent of cations, between 10.0 and 12.5 millimoles of sodium per milliequivalent of cations, or between 10.0 and 15.0 millimoles of sodium per milliequivalent of cations.

Generally, about 0.6-millimoles of total acetate (sodium acetate+acetic acid) in the recharge solution is required per millimole of total $CO_2$ ($CO_2+HCO_3^-+CO_3^{2-}$) that is fed through the zirconium phosphate during therapy in order to achieve the desired effluent pH profile during the next dialysis session. In certain embodiments, the total millimoles of acetate pumped through the zirconium phosphate module during recharging can be between 0.3 and 1.0 millimoles of acetate per millimole of total $CO_2$, between 0.3 and 0.5 millimoles of acetate per millimole of total $CO_2$, between 0.5 and 0.7 millimoles of acetate per millimole of total $CO_2$, or between 0.6 and 1.0 millimoles of acetate per millimole of total $CO_2$.

As described, the patient acidotic state can be used to determine a desired zirconium phosphate effluent pH for a future therapy session. For alkalotic patients, a lower initial therapy zirconium phosphate effluent pH can be selected to minimize the amount of bicarbonate formed from the patient's urea. The initial therapy zirconium phosphate effluent pH depends on the concentrations and volume of recharge solutions used, and can be used by the control system in determining a volume and/or concentration of the recharge solutions.

The amount of recharge solution needed can also depend on the temperature of the recharge solution. The recharging flow paths described can include a heater and optionally a heat exchanger for heating the recharge solution to a specified temperature prior to pumping the recharge solution through the zirconium phosphate module, as recharging zirconium phosphate may be more efficient at elevated temperatures. A temperature sensor determines the temperature of the recharge solution, and the control system can take temperature into account in determining the total amount of recharge solution necessary. The recharge solution can be heated to any specified temperature, including between 60-90° C., 60-70° C., 60-80° C., 75-85° C., or 80-90° C. During recharging, the control system can use only the volume of recharge solution necessary based on the total amount of cations loaded onto the zirconium phosphate, the concentration of the recharge solution, and the temperature of the recharge solution, saving on costs and materials.

Generally, about 6.7 moles of sodium hydroxide is required to recharge the zirconium oxide per mole of phosphate fed through the zirconium oxide module during a previous dialysis session. In certain embodiments, the total moles of sodium hydroxide pumped through the zirconium oxide module during recharging can be between 5.0 and 8.4 moles of sodium hydroxide per mole of phosphate, between 5.0 and 6.5 moles of sodium hydroxide per mole of phosphate, between 6.0 and 7.0 moles of sodium hydroxide per mole of phosphate, between 6.0 and 8.0 moles of sodium hydroxide per mole of phosphate, or between 6.5 and 8.4 moles of sodium hydroxide per mole of phosphate.

The total cations and total $CO_2$ pumped through the zirconium phosphate during a dialysis session can be obtained by direct measurement with one or more sensors in a dialysate flow path during treatment, or estimated. The estimates of total cations and total $CO_2$ can be based on patient weight, the dialysate prescription, pre-dialysis patient cation measurements and/or pre-dialysis patient total $CO_2$ measurements, or any combination thereof. Similarly, the total phosphate pumped through the zirconium oxide during a dialysis session can be obtained by direct measurement by a sensor in the dialysate flow path or estimated based on phosphate bleed from the zirconium phosphate and pre-dialysis patient phosphate measurements. In certain embodiments, the total cations, total $CO_2$, and total phosphate pumped through the sorbent materials can be estimated based on a number of previous dialysis sessions. The values or parameters used can be tracked for a patient over any number of previous dialysis sessions and used to estimate the total cations and total $CO_2$ pumped through the zirconium phosphate in the immediately prior dialysis session. The number of previous dialysis sessions used can be any number n of previous dialysis sessions, where n is 1 or greater. In certain embodiments, the number of previous dialysis sessions can be between 1-5, 2-10, 5-10, or greater number of dialysis sessions. The number of previous dialysis sessions can also be set as a length of time, including dialysis sessions over the prior week, month, year, or any other length of time.

In a non-limiting embodiment, the total urea removed by the zirconium phosphate can be given by EQ(1).

$$\text{Total urea} = Q_d * t * \overline{C}_{Durea} \qquad \text{EQ(1)}$$

Where $Q_d$ is the dialysate flow rate, t is the length of the previous dialysis session, and $\overline{C}_{Durea}$ is the average urea concentration in the dialysate. As described, the average urea concentration of the dialysate can be measured directly by a sensor in the dialysate flow path, or can be estimated. EQ(2) provides an alternative method for determining the amount of urea removed by the zirconium phosphate.

$$\text{Total urea} = V_{prp} * C_{Burea,prp} - V_{post} * C_{Burea,post} \qquad \text{EQ(2)}$$

Where $V_{prp}$ is a patient water volume prior to the dialysis session, $V_{post}$ is the patient water volume after the dialysis session, $C_{Burea,prp}$ is the patient blood urea level prior to the dialysis session, and $C_{Burea,post}$ is the patient blood urea level after the dialysis session. The patient water volume before the dialysis session can be measured via bioimpedance, or estimated based on the patient weight. After the dialysis session, the patient water volume can be measured by bioimepedance, estimated based on weight, or determined by the pre-session patient water volume minus the total ultrafiltration during the dialysis session. The patient blood urea level prior to the dialysis session can be measured directly in the patient's blood, or can be estimated based on populations averages and then adjusted for a specific patient. The patient blood urea level prior to the dialysis session can also be estimated based on therapy frequency or the day of the week. The post-dialysis session blood urea level can be measured directly, or estimated based on the pre-dialysis blood urea level and the urea reduction ratio (URR), where URR is given by EQ(3).

$$URR = 1 - \frac{CBurea, post}{CBurea, prp} \text{ or } C_{Burea,post} = URR * C_{Burea,prp} \qquad \text{EQ (3)}$$

The URR can be estimated based on the patient volume, the dialyzer clearance, and the length of the session, as provided by EQ(4).

$$URR = 1 - e^{-kt/V} \qquad \text{EQ(4)}$$

Where k is the dialyzer clearance, t is the session time, and v is the patient volume. The dialyzer clearance can be determined using EQ(5).

$$k = \frac{e^s - 1}{\frac{e^s}{Q_B} - \frac{1}{Q_d}}; S = \frac{K_o A \left(1 - \frac{Q_B}{Q_D}\right)}{Q_B} \qquad \text{EQ (5)}$$

Where $Q_B$ is the blood flow rate during the dialysis session, $Q_D$ is the dialysate flow rate during the dialysis session, and $K_o A$ is the dialyzer mass transfer coefficient, which can be obtained from the dialyzer spec sheet.

EQ(6) provides a non-limiting equation for determining the total calcium removed by the zirconium phosphate.

$$\text{Total calcium} = Q_d * t * \overline{C}_{D,Ca} \qquad \text{EQ(6)}$$

Where $Q_d$ is the dialysate flow rate, t is the length of the previous dialysis session, and $\overline{C}_{D, Ca}$ is the average calcium concentration in the dialysate entering the sorbent cartridge. The average calcium concentration of the dialysate can be measured directly by a sensor in the dialysate flow path, or can be estimated to be the dialysate prescription level. The total magnesium removed by the zirconium phosphate can be determined in the same manner as the total calcium. The total potassium removed by the zirconium phosphate can be determined in the same way as the total calcium, plus additional potassium from the patient, which can be estimated based on patient blood measurements or assumed using the pre-therapy potassium blood levels.

EQ (7) provides a non-limiting example of an equation for calculating a necessary amount of recharge solution for recharging zirconium phosphate.

$$V_r = v * Q * t * (C_{NH4} + C_K + C_{Ca} + C_{Mg} + (a * C_{HCO3} + b)) \qquad \text{EQ(7)}$$

Where Vr is the volume of recharge solution necessary to recharge the zirconium phosphate, Q is the time averaged volume flow rate into the zirconium phosphate sorbent module, t is the session time, $C_{NH4}$, $C_K$, $C_{Ca}$, $C_{Mg}$, and $C_{HCO3}$ are average concentrations of ammonium ions, potassium ions, calcium ions, magnesium ions and bicarbonate ions entering the zirconium phosphate sorbent module, a and b are variables related to the pH of the zirconium phosphate and relate to an amount of hydrogen released from the zirconium phosphate, and v is a variable specific to the recharge process being used. In the case of recharging with a recharge solution having 4.7 M NaCl, 0.4 M sodium acetate, and 0.4 M acetic acid at 80° C., v=1.10, a=0.14 and b=9.21. One of skill in the art will understand that the values of a, b, and v can be readily derived based on the pH of the zirconium phosphate and the specific conditions being used for recharging.

The values for the concentrations used in EQ(7) can be determined from basic transport models across the dialyzer and mass balance equations, such as those shown in EQ's (1-6), on the dialysate circuit used and are readily derived by those skilled in the art. The transport model across the dialyzer can include the dialysate flow rate, blood flow rate, dialyzer size and koA, pre-dialysis patient levels of the solutes, concentrations in the dialysate for the solutes, patient weight and volume, and ultrafiltration rate. The mass balance on the dialysate circuit can include the concentration of the solutes in the spent dialysate (determined from the dialyzer transport model), the volume of source water used, and the starting water quality, which includes the concentrations of the solutes in the starting water used to generate the initial dialysate. The pre-dialysis patient levels of the solutes or the patient acidotic state can be measured with a blood analyzer before the treatment or can be estimated based on the patient's dialysis schedule and typical session parameters like frequency per week, session time, patient weight, patient acidotic state, and time since last session. The methods to estimate the concentration from these values can be derived by one skilled in the art.

As described, specific alarms or instances during treatment can also affect the concentration and volume of the recharge solution necessary for recharging the sorbent modules. Ammonia breakthrough could indicate that the zirconium phosphate was fully loaded with cations, and the recharge volume may be increased accordingly. For example, if ammonia breakthrough occurs, 7.0 L of a recharge solution having 4.7 M NaCl, 0.4 M sodium acetate, and 0.4 M acetic acid can be used to recharge the zirconium phosphate. Alternatively, the total concentrations of sodium and acetate in the recharge solution can be increased and the volume of recharge solution kept the same. In certain embodiments, the volume and/or concentration of the recharge solution can be increased beyond that required for recharging the sorbent material to ensure complete recharging.

A pH alarm could indicate that the zirconium phosphate was fully titrated with bicarbonate during treatment, and the recharge solution volume or concentration should be increased accordingly. For example, 7.0 L of a recharge solution having 4.7 M NaCl, 0.4 M sodium acetate, and 0.4 M acetic acid can be used to recharge the zirconium phosphate in the event of a pH alarm, or the concentrations of acetate in the recharge solution increased.

A blood leak could result in a need to increase the volume of disinfect solution needed to fully disinfect the zirconium phosphate or zirconium oxide or to compensate for less efficient recharge due to more protein exposure of the zirconium phosphate. In certain embodiments, 0.1 L extra of disinfectant solution can be used for each instance of a blood leak during treatment, depending on the disinfectant used and the concentration.

In certain embodiments, an estimated duration to a next dialysis session for the patient can be used in setting the recharge solution volume and/or concentration. If the duration to the next dialysis session will be longer, the patient may have a higher urea level and a higher phosphate level at the start of the next dialysis session, and a higher capacity required for the zirconium phosphate and zirconium oxide. In such instances, the volume and/or concentration of the recharge solutions can be increased to compensate for the expected higher requirements in the next dialysis session.

Given that about 6.7 moles of sodium hydroxide is required to recharge the zirconium oxide per mole of phosphate fed through the zirconium oxide module during a previous dialysis session, a person of ordinary skill can calculate the total volume of sodium hydroxide necessary for recharging. For example, if 10 moles of phosphate are fed through the zirconium oxide module during a previous dialysis session, about 67 moles of sodium hydroxide will be required for recharging.

Figure 6:
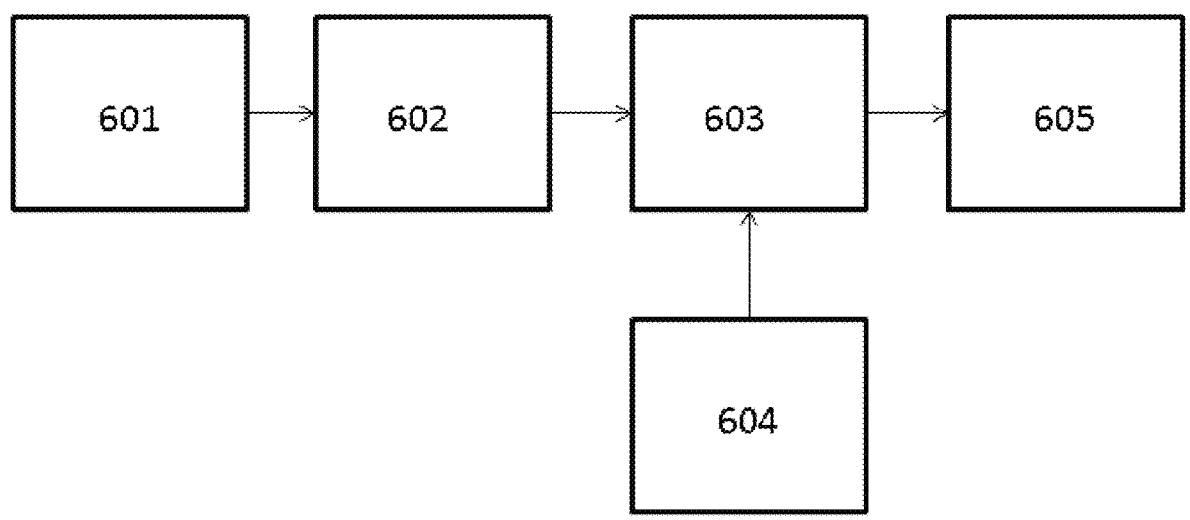
FIG. 6 is a flow chart illustrating the steps in customizing a zirconium phosphate recharging process.

FIG. 6 is a flow chart illustrating the steps in customizing a zirconium phosphate recharging process based. In step 601, a desired initial therapy zirconium phosphate effluent pH can be determined. As described, the desired initial therapy zirconium phosphate effluent pH can be based on one or more patient parameters and system parameters, including the patient's pre-treatment bicarbonate and urea levels, as well as the available of additional bicarbonate to be added during dialysis and the degassing capabilities of the system. The desired initial therapy zirconium phosphate effluent pH can be determined by the control system based on the patient parameters and/or system parameters, or directly entered by a user through a user interface. In step 602 the concentrations of acid, base, and sodium salt in the recharge solution can be determined. The described concentrations depend on the pKa of the acid or buffer, the buffer capacity, and the temperature of the recharge solution, and can be automatically determined by the control system. Where a single recharge solution source is used, the control system can automatically inform the user to add a specific amount of acid, base, or salt to the recharge solution. Where two or more recharge solution sources are used, the control system can determine the relative amounts of fluid needed from each recharge solution source.

In step 604, the system can determine an amount of cations removed by the zirconium phosphate module in a previous dialysis session. The amount of cations removed by the zirconium phosphate module depends on the pre-dialysis patient potassium, calcium, magnesium, and urea levels of the patient, as well as patient weight, patient bicarbonate level, dialysate flow rate, blood flow rate, dialyzer size, dialysis time, ultrafiltration rate, and the potassium, calcium, magnesium, and bicarbonate dialysis prescription. The described patient parameters can automatically be received by the control system through a tracking device on the zirconium phosphate module tracking usage. Alternatively, the described patient parameters can be input directly by the user based on the patient's medical records or other information. The described patient parameters can also be assumed by the system based on patient norms and settings entered into the system based on patient blood labs.

In step 603, the amount of acid, base, and sodium salt necessary to achieve the desired initial therapy zirconium phosphate effluent pH can be determined. Using the total volume determined in step 604, and the concentrations determined in step 602, the control system can automatically determine the pump rates and/or valve switching necessary to recharge the zirconium phosphate from one or more recharge solution sources and control the pumps and valves to generate the recharge solution. In step 605, the control system controls the pumps and valves to recharge the zirconium phosphate module.

One of skill in the art will understand that one or more of the steps illustrated in FIG. 6 can be eliminated. For example, if a desired initial therapy zirconium phosphate effluent pH of 6.5 will be used for nearly all patients, the system can skip steps 601 and 602. The concentrations of the acid, base, and salt necessary to generate a recharge solution with the correct pH can be stored in a system memory and used each time. If a specified recharge solution volume is used each time, step 604 can also be eliminated.

One skilled in the art will understand that various combinations and/or modifications and variations can be made in the described systems and methods depending upon the specific needs for operation. Moreover, features illustrated or described as being part of an aspect of the invention may be used in the aspect of the invention, either alone or in combination, or follow a preferred arrangement of one or more of the described elements.

We claim:

1. A method, comprising the steps of:
   recharging a sorbent material within a sorbent module (402, 702) by pumping one or more recharge solutions through the sorbent module;
   wherein a volume and/or a concentration of the one or more recharge solutions is set based on one or more patient parameters and/or one or more dialysis session parameters for a patient and/or dialysis session using the sorbent module.

2. The method of claim 1, wherein the sorbent module contains zirconium oxide, and wherein the one or more patient parameters and/or one or more dialysis session parameters include a total phosphate pumped through the sorbent module during a prior dialysis session.

3. The method of claim 2, wherein the total cation and total $CO_2$ pumped through the sorbent module is obtained from any of:
   a. direct measurement of total cations and total $CO_2$ in a dialysate flow path during the prior dialysis session;
   b. estimation of total cations and total $CO_2$ based on patient weight;
   c. estimation of total cations and total $CO_2$ based on a dialysis prescription;
   d. estimation of total cations and total $CO_2$ based on pre-dialysis patient cation measurements and/or pre-dialysis patient total $CO_2$ measurements;
   e. estimation of total cations and total CO2 based on a number of previous dialysis sessions; or
   f. combinations thereof.

4. The method of claim 2, wherein the step of recharging the zirconium phosphate comprises pumping:
   (a) between 5.0 and 6.0 millimoles of sodium in the one or more recharge solutions per total milliequivalents of total cations pumped through the sorbent module during the prior dialysis session; or
   (b) between 0.3 and 1.0 millimoles of acetate in the one or more recharge solutions per millimole of total $CO_2$ pumped through the sorbent module during the prior dialysis session.

5. The method of claim 2, wherein the total phosphate pumped through the sorbent module during the prior dialysis session is obtained from direct measurement of phosphate in a dialysate flow path during the prior session, estimated based on phosphate bleed from zirconium phosphate used in the prior dialysis session and pre-dialysis patient phosphate measurements, or estimated based on a total phosphate pumped through the sorbent cartridge in a number of previous dialysis sessions.

6. The method of claim 2, wherein the step of recharging the zirconium oxide comprises pumping between 6.0 and 7.5 moles of sodium hydroxide in the one or more recharge solutions per mole of phosphate pumped through the sorbent module during the prior dialysis session.

7. The method of claim 1, wherein the one or more patient parameters and/or one or more dialysis session parameters include an estimated duration to a next dialysis session for the patient.

8. The method of claim 1, wherein the sorbent module contains zirconium phosphate, and wherein the volume of the one or more recharge solutions is set using an equation $V_r = v*Q*t*(C_{NH4}+C_K+C_{Ca}+C_{Mg}+(a*C_{HCO3}+b))$; wherein Vr is the volume of the one or more recharge solutions, Q is a time averaged volume flow rate into the sorbent module, t is a session time, $C_{NH4}$, $C_K$, $C_{Ca}$, $C_{Mg}$, and $C_{HCO3}$ are average concentrations of ammonium ions, potassium ions, calcium ions, magnesium ions and bicarbonate ions entering the sorbent module, a and b are variables related to a pH of the zirconium phosphate, and v is a variable specific to a recharge process being used.

9. A system comprising:
   a recharging flow path (401, 701); the recharging flow path comprising one or more recharge solution sources; the one or more recharge solution sources (405, 406, 705) fluidly connectable to an inlet (403, 703) of a sorbent module (402, 702) containing at least one sorbent material; and at least one pump (407, 706) for pumping one or more recharge solutions from the one or more recharge solution sources through the sorbent module; and
   a control system, the control system setting a volume and/or concentration of the one or more recharge solutions pumped through the sorbent module necessary to recharge the sorbent material within the sorbent module based on one or more patient parameters and/or one or more dialysis session parameters for a patient and/or dialysis session using the sorbent module.

10. The system of claim 9, wherein:
    the sorbent module (401) contains zirconium phosphate, and wherein the one or more recharge solution sources comprise a brine source (405), a water source, and a disinfectant source; or
    wherein the sorbent module contains zirconium oxide (702), and wherein the one or more recharge solution sources comprise a base source (705), a water source, and a disinfectant source.

11. The system of claim 9, further comprising a second recharging flow path; the second recharging flow path comprising one or more recharge solution sources fluidly connectable to an inlet of a second sorbent module containing at least one sorbent material; and at least a second pump for pumping one or more recharge solutions from the one or more recharge solution sources through the sorbent module;
    wherein the control system sets a volume and/or concentration of the one or more recharge solutions pumped through the second sorbent module necessary to recharge the sorbent material within the second sorbent module based on the one or more patient parameters and/or one or more dialysis session parameters for the patient and/or dialysis session using the sorbent module.

12. The system of claim 9, wherein the sorbent module contains zirconium phosphate,
    wherein the one or more patient parameters include at least one from a group consisting of: pre-dialysis patient potassium, calcium, magnesium, bicarbonate and urea levels, patient weight, patient volume, patient residual kidney function, patient acidotic state, an average number of dialysis sessions per week, and an average dialysis session length; and
    wherein the one or more dialysis session parameters include at least one from a group consisting of: dialysate flow rate, blood flow rate, dialyzer size, dialyzer type, dialysis time, ultrafiltration rate, a potassium, calcium, magnesium, and bicarbonate dialysis prescription, whether ammonia breakthrough occurred, whether a pH alarm occurred, fluid removed during a session, total volume treated, starting water quality, URR target, URR achieved, clearance, whether a blood leak occurred, and whether a hypotensive episode occurred.

13. The system of claim 9, wherein the sorbent module contains zirconium oxide, wherein the one or more patient parameters include at least one from a group consisting of: patient weight, patient volume, patient residual kidney function, an average number of dialysis sessions per week, and an average dialysis session length; and wherein the one or more dialysis session parameters include at least one from a group consisting of: dialysate flow rate, blood flow rate, dialyzer size, dialyzer type, dialysis time, ultrafiltration rate, a potassium, calcium, magnesium, and bicarbonate dialysis prescription, whether ammonia breakthrough occurred, whether a pH alarm occurred, fluid removed during a session, total volume treated, starting water quality, URR target, URR achieved, clearance, whether a blood leak occurred, and whether a hypotensive episode occurred.

14. The system of claim 9, wherein:

the sorbent module contains zirconium phosphate, and wherein the control system sets the volume and/or concentration of the one or more recharge solutions based on a total cation and total $CO_2$ pumped through the sorbent module during a prior dialysis session; or wherein the sorbent module contains zirconium oxide, and wherein the control system sets the volume and/or concentration of the one or more recharge solutions based on a total phosphate pumped through the sorbent module during a prior dialysis session.

* * * * *